US010016314B2

(12) United States Patent
Eckstein et al.

(10) Patent No.: US 10,016,314 B2
(45) Date of Patent: Jul. 10, 2018

(54) APPARATUS AND METHOD FOR MANUFACTURING ABSORBENT ARTICLES

(71) Applicant: The Procter & Gamble Company, Cincinnati, OH (US)

(72) Inventors: Joseph Allen Eckstein, Sunman, IN (US); Uwe Schneider, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 690 days.

(21) Appl. No.: 14/642,809

(22) Filed: Mar. 10, 2015

(65) Prior Publication Data
US 2015/0257941 A1   Sep. 17, 2015

Related U.S. Application Data

(60) Provisional application No. 61/953,957, filed on Mar. 17, 2014.

(51) Int. Cl.
*A61F 13/15* (2006.01)
*B65H 19/12* (2006.01)
(Continued)

(52) U.S. Cl.
CPC ....... *A61F 13/15764* (2013.01); *B65H 19/12* (2013.01); *B65H 49/12* (2013.01);
(Continued)

(58) Field of Classification Search
CPC ........ B65H 67/02; B65H 49/12; B65H 19/12; B65H 2701/319; B65H 2301/41828;
(Continued)

(56) References Cited

U.S. PATENT DOCUMENTS 1,459,694 A   6/1923   Holder
1,578,488 A   3/1926   Howard
(Continued)

FOREIGN PATENT DOCUMENTS

BE   1 009 581 A3   5/1997
CH   223 815 A    10/1942
(Continued)

OTHER PUBLICATIONS

PCT/US2015/019596 International Search Report, dated Jun. 23, 2015, 11 pages.

*Primary Examiner* — William Arauz Rivera
(74) *Attorney, Agent, or Firm* — Sarah M. DeCristofaro

(57) ABSTRACT

An apparatus and method for loading material may utilize an unwind apparatus and a loading apparatus. The unwind apparatus may include a frame and a mandrel. The mandrel may be adapted to receive a spool including a core and a strand of material. The mandrel may be associated with a mandrel support member, which provides support. The loading apparatus includes a base member and a loading shaft having a proximal end portion and a distal end portion. The proximal end portion may be connected with the base member and the distal end portion may be configured to engage the mandrel. The loading shaft may support a replacement spool including a core and a strand of material wound around the core. When the loading shaft is engaged with the mandrel, the core of the replacement spool is movable from the loading shaft to the mandrel.

17 Claims, 16 Drawing Sheets

(51) Int. Cl.
*B65H 49/12* (2006.01)
*B65H 67/02* (2006.01)

(52) U.S. Cl.
CPC ... *B65H 67/02* (2013.01); *B65H 2301/41745* (2013.01); *B65H 2301/41828* (2013.01); *B65H 2701/319* (2013.01); *B65H 2801/57* (2013.01)

(58) Field of Classification Search
CPC ...... B65H 2301/41745; B65H 2801/57; A61F 13/15764
See application file for complete search history.

(56) References Cited

U.S. PATENT DOCUMENTS

| | | | |
|---|---|---|---|
| 2,561,543 A * | 7/1951 | Teplitz | B21C 47/34 242/559.3 |
| 2,602,606 A | 7/1952 | Hanse | |
| 2,809,791 A | 10/1957 | Haworth | |
| 2,942,802 A | 6/1960 | Bachus | |
| 3,073,545 A | 1/1963 | Frate et al. | |
| 3,150,845 A | 9/1964 | Pool | |
| 3,175,784 A | 3/1965 | Dambrogio | |
| 3,315,917 A | 4/1967 | Brown | |
| 3,428,269 A | 2/1969 | Horwood et al. | |
| 3,637,155 A | 1/1972 | Pato | |
| 3,847,366 A * | 11/1974 | Schmidt | B29C 53/32 242/530.4 |
| 3,860,003 A | 10/1975 | Buell | |
| 4,074,871 A | 2/1978 | Stotler | |
| 4,100,721 A | 7/1978 | Seiichi et al. | |
| 4,180,218 A | 12/1979 | Jacobs | |
| 4,235,393 A | 11/1980 | Schenkel et al. | |
| 4,298,174 A | 11/1981 | Kovaleski | |
| 4,402,467 A | 9/1983 | Kontz | |
| 4,515,328 A | 5/1985 | Payne, Jr. | |
| 4,610,678 A | 9/1986 | Weisman et al. | |
| 4,673,140 A | 6/1987 | Boles | |
| 4,673,402 A | 6/1987 | Weisman et al. | |
| 4,687,151 A | 8/1987 | Memminger et al. | |
| 4,695,278 A | 9/1987 | Lawson | |
| 4,704,115 A | 11/1987 | Buell | |
| 4,795,454 A | 1/1989 | Dragoo | |
| 4,834,735 A | 5/1989 | Alemany et al. | |
| 4,888,231 A | 12/1989 | Angstadt | |
| 4,909,803 A | 3/1990 | Aziz et al. | |
| 5,031,381 A * | 7/1991 | Focke | B65H 19/123 242/559.2 |
| 5,562,646 A | 10/1996 | Goldman et al. | |
| 5,599,335 A | 2/1997 | Goldman et al. | |
| 5,628,097 A | 5/1997 | Curro et al. | |
| 5,669,894 A | 9/1997 | Goldman et al. | |
| 5,692,698 A | 12/1997 | Forbes | |
| 5,709,354 A | 1/1998 | Blandin et al. | |
| 5,749,210 A | 5/1998 | Kikuchi et al. | |
| 5,803,652 A * | 9/1998 | Martin | B23Q 3/186 242/533.7 |
| 5,916,661 A | 6/1999 | Curro et al. | |
| 5,975,457 A | 11/1999 | Forbes | |
| 6,056,232 A * | 5/2000 | Karaki | G03B 17/26 242/559.3 |
| 6,076,763 A | 6/2000 | Sparafora | |
| 6,107,539 A | 8/2000 | Palumbo et al. | |
| 6,386,477 B1 | 5/2002 | Kaufmann et al. | |
| 6,533,212 B1 | 3/2003 | Tafel, II | |
| 6,545,197 B1 | 4/2003 | Mueller et al. | |
| 6,676,054 B2 | 1/2004 | Heaney et al. | |
| 6,722,606 B2 | 4/2004 | Hanson et al. | |
| 6,786,264 B1 | 9/2004 | Torres Martinez | |
| 6,790,798 B1 | 9/2004 | Suzuki | |
| 6,820,837 B2 | 11/2004 | Long | |
| 6,923,401 B2 | 8/2005 | Lock | |
| 7,056,076 B2 * | 6/2006 | Ichikawa | B65H 19/123 242/563 |
| 7,527,216 B2 | 5/2009 | Manning, Jr. et al. | |
| 7,540,174 B2 | 6/2009 | Snijders | |
| 7,569,039 B2 | 8/2009 | Matsuda et al. | |
| 7,621,479 B2 | 11/2009 | Matzenmüller | |
| 7,806,360 B2 | 10/2010 | Chadwick | |
| 7,878,447 B2 | 2/2011 | Hartzheim | |
| 7,887,001 B2 | 2/2011 | Yoon et al. | |
| 7,896,282 B2 | 3/2011 | Barea | |
| 7,905,446 B2 | 3/2011 | Hartzheim | |
| 9,067,755 B2 | 6/2015 | Barea | |
| 2004/0097895 A1 | 5/2004 | Busam et al. | |
| 2004/0104299 A1 | 6/2004 | Heaney et al. | |
| 2004/0158212 A1 | 8/2004 | Ponomarenko et al. | |
| 2005/0107764 A1 | 5/2005 | Matsuda et al. | |
| 2005/0133653 A1 | 6/2005 | Heaney et al. | |
| 2005/0150990 A1 * | 7/2005 | Schmidt-Hebbel | B65H 19/12 242/533.7 |
| 2005/0278914 A1 | 12/2005 | Bartkowiak et al. | |
| 2006/0131459 A1 | 6/2006 | Barea | |
| 2007/0084960 A1 | 4/2007 | Heanley et al. | |
| 2009/0312730 A1 | 12/2009 | LaVon et al. | |
| 2011/0042012 A1 | 2/2011 | Benner et al. | |
| 2011/0127364 A1 | 6/2011 | Rees et al. | |
| 2012/0061015 A1 | 3/2012 | LaVon et al. | |
| 2012/0061016 A1 | 3/2012 | LaVon et al. | |
| 2012/0217337 A1 | 8/2012 | Barea | |
| 2013/0112794 A1 | 5/2013 | Castillo et al. | |
| 2013/0112800 A1 | 5/2013 | Castillo et al. | |
| 2013/0161431 A1 | 6/2013 | Yanez, Jr. et al. | |
| 2013/0255861 A1 | 10/2013 | Schneider | |
| 2013/0255862 A1 | 10/2013 | Schneider et al. | |
| 2013/0255863 A1 | 10/2013 | LaVon et al. | |
| 2013/0255864 A1 | 10/2013 | Schneider et al. | |
| 2013/0255865 A1 | 10/2013 | Brown et al. | |

FOREIGN PATENT DOCUMENTS

| | | |
|---|---|---|
| DE | 1 972 011 U | 11/1967 |
| DE | 1 449 659 A1 | 3/1969 |
| DE | 38 33 434 C1 | 12/1989 |
| DE | 102 24 909 A1 | 12/2003 |
| EP | 0 045 854 A1 | 2/1982 |
| FR | 2 104 228 A5 | 4/1972 |
| GB | 598 999 A | 3/1948 |
| GB | 2 172 617 A | 2/1986 |
| JP | 02 11172 U | 1/1990 |
| JP | 06 287843 A | 10/1994 |
| JP | 08 151169 A | 6/1996 |
| JP | 2001 025868 A | 1/2001 |
| JP | 3505856 | 3/2004 |
| WO | WO 89/00971 A1 | 2/1989 |
| WO | WO 02/077685 A1 | 10/2002 |

* cited by examiner

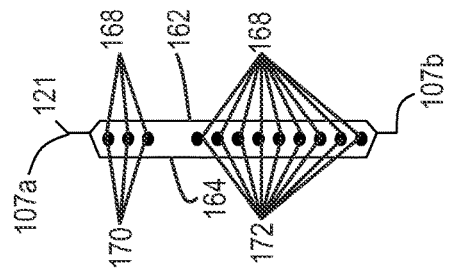
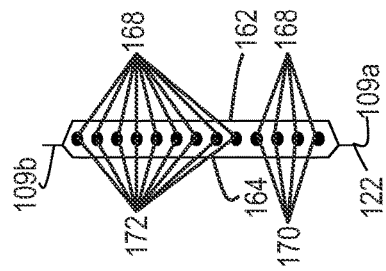
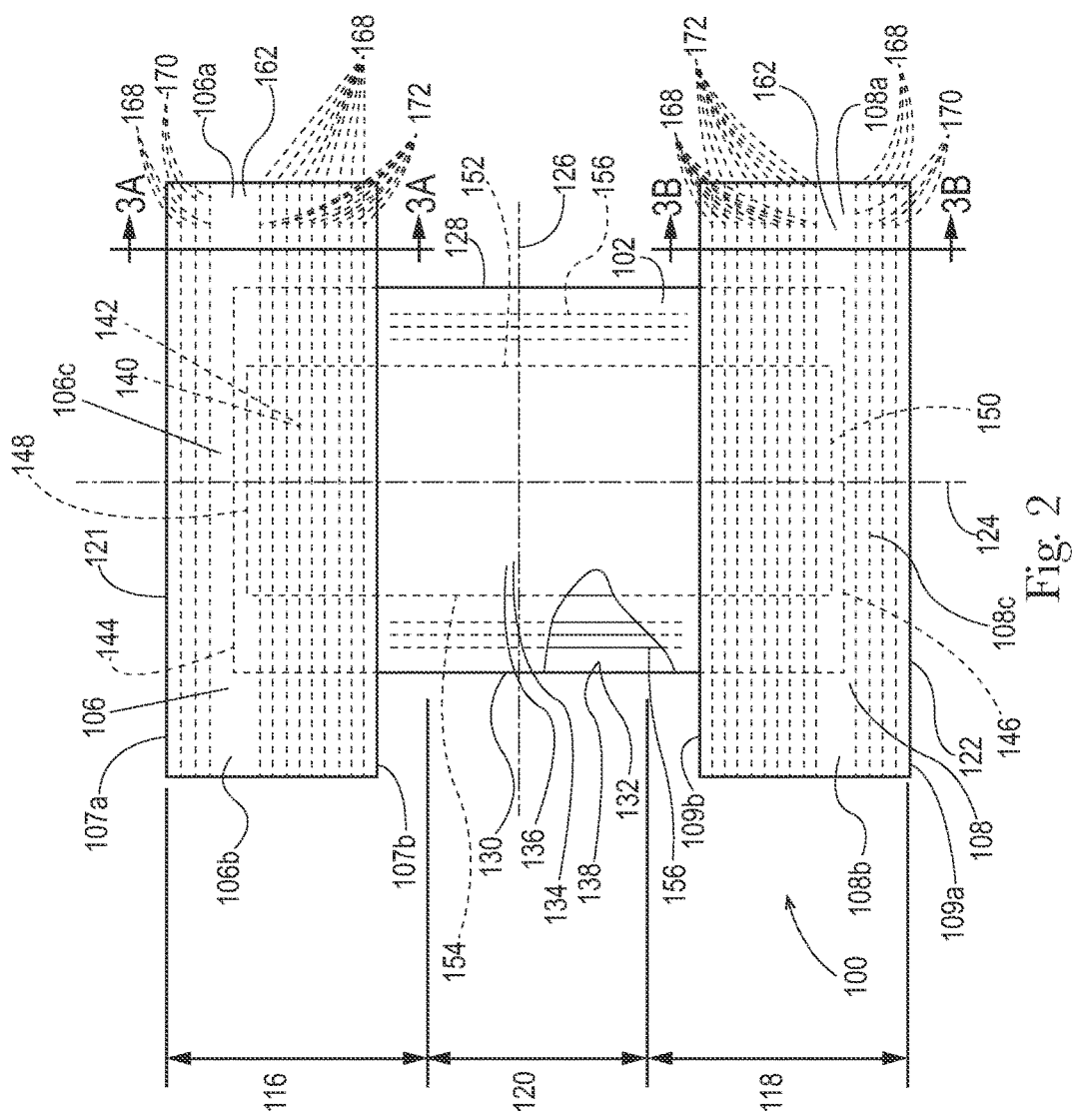

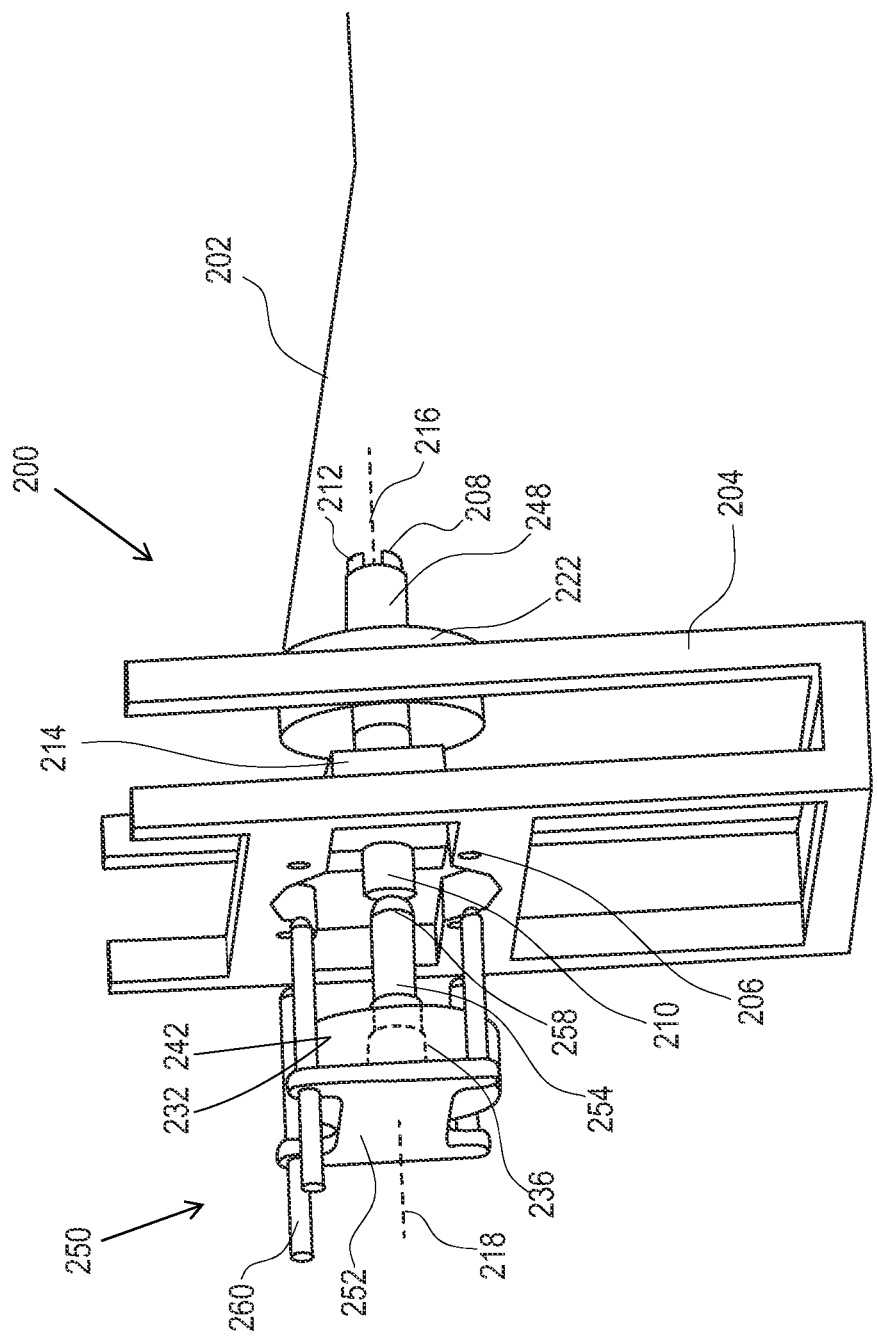

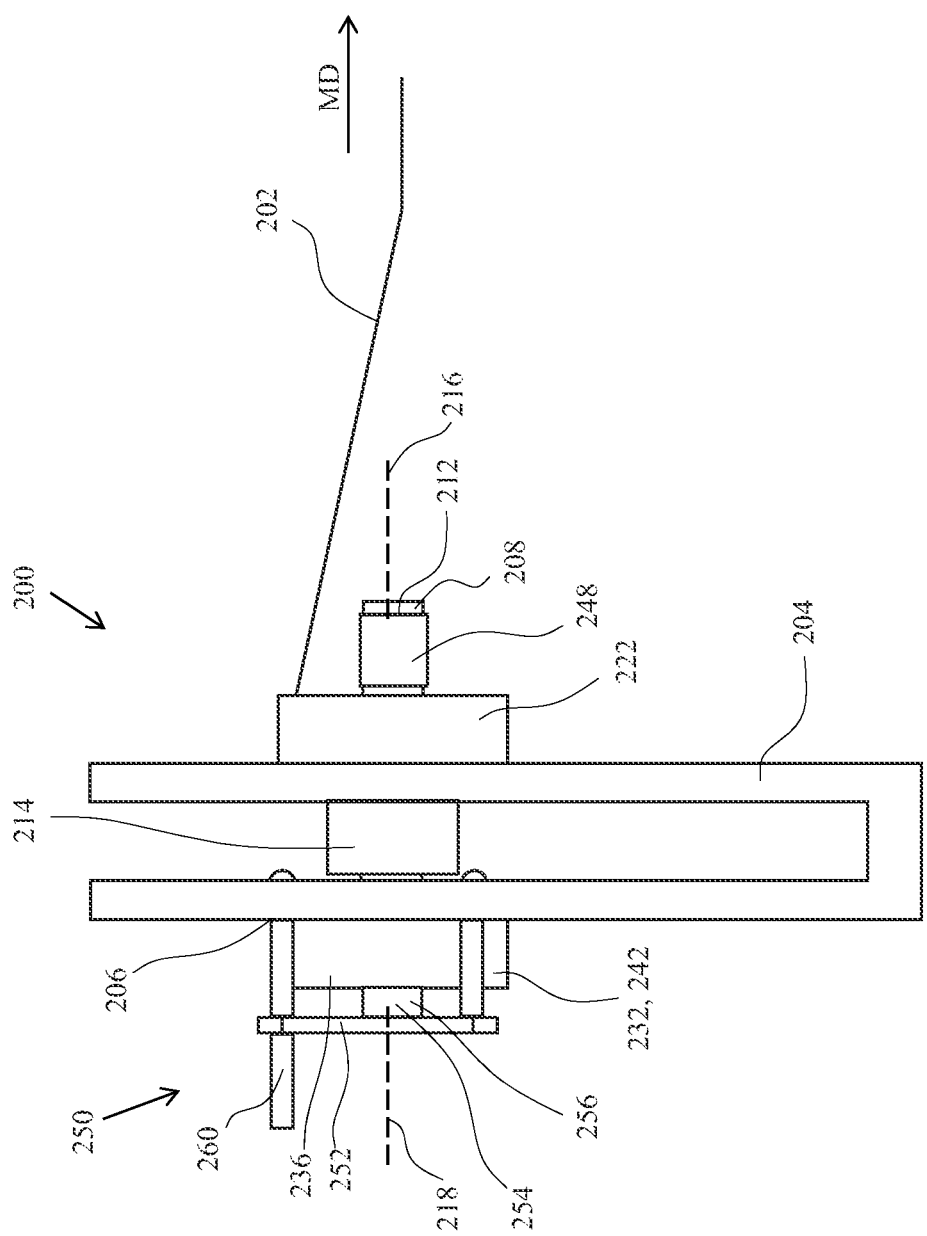

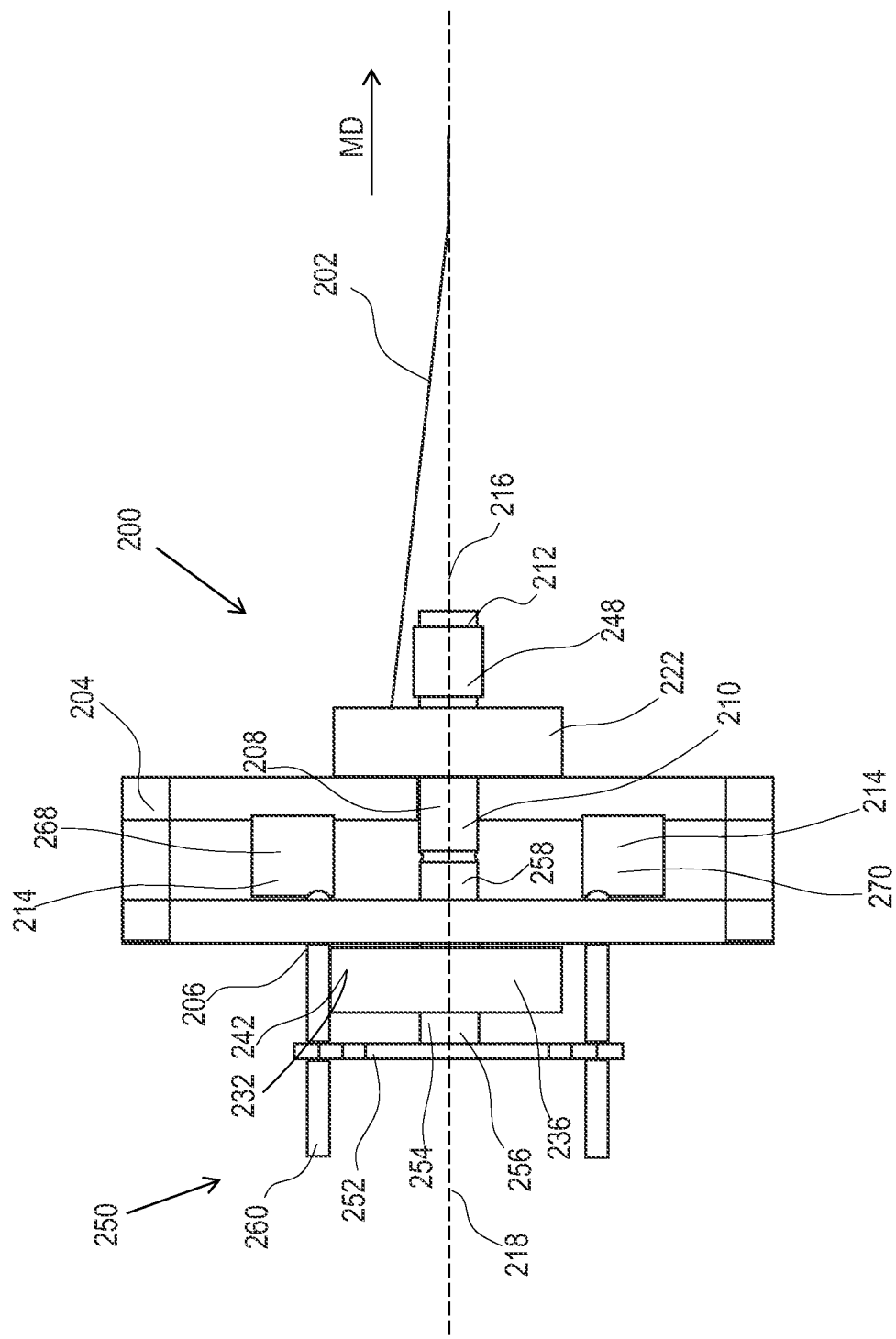

APPARATUS AND METHOD FOR MANUFACTURING ABSORBENT ARTICLES

FIELD OF THE INVENTION

The present disclosure relates to apparatuses and methods for manufacturing absorbent articles, and more particularly, to apparatuses and methods for unwinding material used in absorbent articles.

BACKGROUND OF THE INVENTION

Along an assembly line, diapers and various types of other absorbent articles may be assembled by adding components to and otherwise modifying an advancing, continuous web of material. For example, in some processes, advancing webs of material are combined with other advancing webs of material. In other examples, individual components created from advancing webs of material are combined with advancing webs of material, which in turn, are then combined with other advancing webs of material. Webs of material and component parts used to manufacture diapers may include: backsheets, topsheets, absorbent cores, front and/or back ears, fastener components, and various types of webs, including elastic webs, and components such as leg elastics, barrier leg cuffs, and waist elastics. Once the desired component parts are assembled, the advancing web(s) and component parts are subjected to a final knife cut to separate the web(s) into discrete diapers or other absorbent articles. The discrete diapers or absorbent articles may also then be folded and packaged.

As stated above, during the assembly process, component parts, such as elastic components, are used to manufacture diapers. Generally, the component parts are supplied on spools that comprise a core and a material wound around the core. Spools used in the manufacture of the absorbent articles are located adjacent to the manufacturing line on unwind stations. Traditionally, the unwind stations are large, occupying a substantial amount of floor space in the manufacturing facility. The large size of the unwind stations is also due in part to the need to operate at high manufacturing speeds and the relatively large amount of component material used in a single absorbent article. In order for manufactures to supply enough material to the manufacturing line, several spools of material must be stored adjacent to the line. Traditionally, unwind stations consist of spools mounted in vertical tiers. Each tier has at least two spools, an active spool and a reserve spool. The spools in the same tier are located adjacent one another in the same horizontal plane.

The active spool is unwound such that the elastic material may be fed through a control device such as a metering device or tension device. The control device is positioned between the active and reserve spools so that the elastic material is unwound at an angle. More specifically, the cores of each of the active spool and the reserve spool are not parallel to the control device. Having each spool at an angle to the control device allows manufacturers to switch to the reserve spool after the active spool has been depleted. For seamless transitions, manufactures connect the end of the active spool to the beginning of the reserve spool. The empty spool can then be removed and replaced with a new reserve spool. Thus, the unwind stations have to have sufficient room to load and unload the spools. The spools are loaded and unloaded by threading the core of the spool onto a spool holder, which is generally a fixed shaft. More specifically, the spool holder has an open portion adjacent to the control device where a spool can be loaded adjacent to the control device.

However, the use of unwind devices similar to the aforementioned have presented several problems. For example, unwind stations must be of sufficient size to handle multiple, vertical tiers of spools and tiers having at least an active spool and a replacement spool located horizontally and adjacent to one another. Thus, unwind stations have been large, taking up relatively large amounts of floor space in manufacturing facilities. Further, unwind stations must have sufficient room for operators to load and unload the spools from the portion of the spool holder adjacent to the control system. Further still, operators are required to load the unwind stations near the active unwinding of material. Thus, operators must be extremely careful when loading and unloading not to disrupt the material that is being unwound on the active spool. A disruption in the material can result in, for example, defective products and manufacturing down time.

Thus, a need exists for a method and an apparatus for unwinding material for absorbent articles that allows for a relatively smaller amount of floor space to be used and allows for loading of the unwinding station while reducing the potential for interfering with the unwinding of the active spool.

SUMMARY OF THE INVENTION

Aspects of the present disclosure relate to an apparatus and method for assembling absorbent articles. The apparatus may include an unwind apparatus and a loading apparatus. The unwind apparatus may include a frame and a mandrel. The mandrel may include a proximal end portion and a distal end portion and be adapted to support a spool comprising a core and a strand of material wound around the core. More specifically, the mandrel is adapted to be received by the core of the spool. A mandrel support member may be associated with the mandrel and may be moveable with respect to the frame. Further, the apparatus may include a loading apparatus for supporting a replacement spool including a core and a strand of material wound around the core. The loading apparatus may comprise a base member and a loading shaft. The loading shaft may include a proximal end portion and a distal end portion. The proximal end portion of the loading shaft may be connected with the base member, and the distal end portion may be configured to associate with the proximal end portion of the mandrel. The apparatus may be in a first configuration or a second configuration. In a first configuration, the distal end portion of the loading shaft is slidably engaged with the proximal end portion of the mandrel, and the mandrel support member is disassociated from the mandrel such that the core of the replacement spool is movable along the loading shaft and onto the mandrel. In a second configuration, the distal end portion of the loading shaft is disassociated with the proximal end portion of the mandrel, and the mandrel support member is associated with the mandrel.

In another embodiment, a method for loading material on an unwinding apparatus may comprise the steps of: providing a mandrel including a proximal end portion and a distal end portion, wherein the mandrel is adjacent to a frame, and wherein a portion of the mandrel is associated with a mandrel support member; supporting a first spool on a mandrel, the first spool comprising a first core and a first strand of material wound around the first core, and wherein the first core is adapted to receive the mandrel, and wherein the mandrel; providing a second spool comprising a second core and a second strand of material wound around the second core; placing the second spool onto a loading shaft including a proximal end portion and a distal end portion, wherein the second core is adapted to receive the loading shaft; slidably engaging the loading shaft with the mandrel; disassociating the mandrel support member from the mandrel; moving the second spool axially along the support shaft and onto the mandrel; reassociating the support member with the mandrel; and disengaging the loading shaft from the mandrel.

BRIEF DESCRIPTION OF THE DRAWINGS

FIG. 2 is a partially cut away plan view of the diaper pant shown in FIG. 1;

FIG. 3A is a cross-sectional view of the diaper pant of FIG. 2 taken along line 3A-3A;

FIG. 3B is a cross-sectional view of the diaper pant of FIG. 2 taken along line 3B-3B;

FIG. 6 is a perspective view of an unwind apparatus and a loading apparatus in accordance with one non-limiting embodiment of the present disclosure;

FIG. 7 is a side view of an unwind apparatus and a loading apparatus in accordance with one non-limiting embodiment of the present disclosure;

FIG. 8A is a top view of an unwind apparatus and a loading apparatus in accordance with one non-limiting embodiment of the present disclosure;

DETAILED DESCRIPTION OF THE INVENTION

Figure 1:
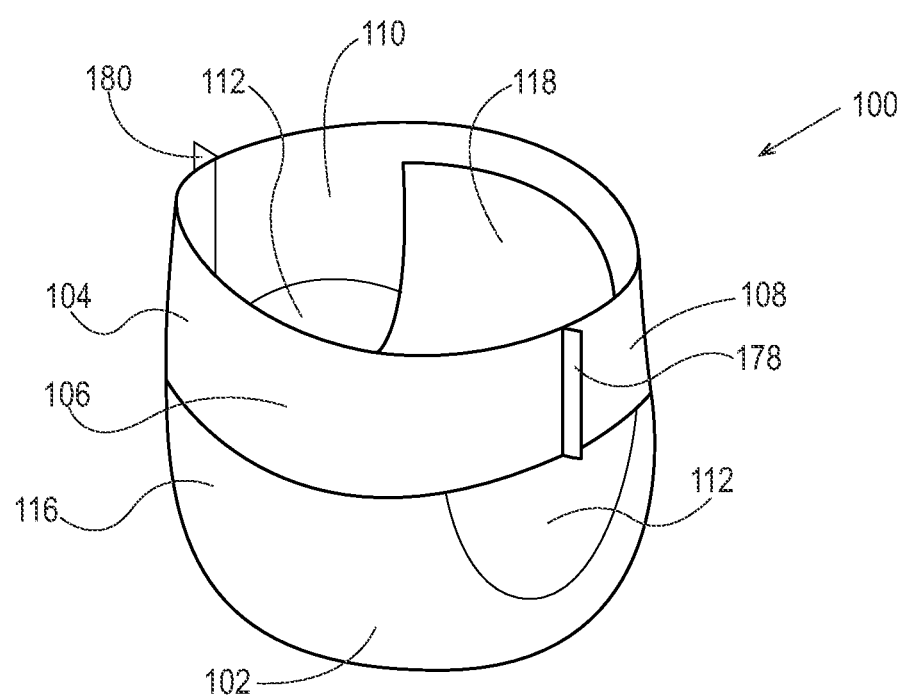
FIG. 1 is a perspective view of a diaper pant.

The following term explanations may be useful in understanding the present disclosure:

"Absorbent article" is used herein to refer to consumer products whose primary function is to absorb and retain soils and wastes. "Diaper" is used herein to refer to an absorbent article generally worn by infants and incontinent persons about the lower torso. The term "disposable" is used herein to describe absorbent articles which generally are not intended to be laundered or otherwise restored or reused as an absorbent article (e.g., they are intended to be discarded after a single use and may also be configured to be recycled, composted or otherwise disposed of in an environmentally compatible manner).

The term "pant" (also referred to as "training pant", "pre-closed diaper", "diaper pant", "pant diaper", and "pull-on diaper") refers herein to disposable absorbent articles having a continuous perimeter waist opening and continuous perimeter leg openings designed for infant or adult wearers. A pant can be configured with a continuous or closed waist opening and at least one continuous, closed, leg opening prior to the article being applied to the wearer.

The term "machine direction" (MD) is used herein to refer to the direction of material flow through a process. In addition, relative placement and movement of material may be described as flowing in the machine direction through a process from upstream in the process to downstream in the process.

The present disclosure relates to a method and apparatus for unwinding spools of material, such as elastic material, for use in absorbent articles. More particularly, the apparatus herein is directed to an unwind apparatus for unwinding a spool of material and a loading apparatus for loading spools of material onto the unwind apparatus. As discussed in more detail below, the unwind apparatus may include a mandrel adapted to support a spool of material, such as elastic material. The mandrel may be substantially surrounded by a frame. Further, the unwind apparatus can be configured to engage with the loading apparatus. The loading apparatus may include a base member and a loading shaft, extending from the base member. The loading shaft may be configured to support a replacement spool of stranded material. The base member may be releasably connectable with the frame of the unwind apparatus. As discussed in more detail below, the unwind apparatus and the loading apparatus may be reconfigurable. For example, in a first configuration, the loading apparatus may be engaged with the unwind apparatus such that a replacement spool may be moved from the loading apparatus to the unwind apparatus. In a second configuration, the loading apparatus may be disengaged with the unwind apparatus, and the mandrel may support one or more spools of material.

It is to be appreciated that various arrangements and configurations of the apparatus herein may be used to load and unwind various types of materials. For example, as discussed in more detail below, the apparatus according to the present disclosure may be utilized in the production of various components of absorbent articles, such as diapers. For example, webs of material and component parts used to manufacture diapers may include: backsheets, topsheets, absorbent cores, front and/or back ears, fastener components, and various types of webs, including elastic webs, and components such as leg elastics, barrier leg cuffs elastics, and waist elastics. To help provide additional context to the subsequent discussion of the process embodiments, the following provides a general description of absorbent articles in the form of diapers that include components including the materials that may be supplied by the methods and apparatuses disclosed herein.

FIGS. 1 and 2 show an example of a diaper pant 100 that may be assembled with the apparatuses and methods disclosed herein. In particular, FIG. 1 shows a perspective view of a diaper pant 100 in a pre-fastened configuration, and FIG. 2 shows a plan view of the diaper pant 100 with the portion of the diaper that faces away from a wearer oriented towards the viewer. The diaper pant 100 shown in FIGS. 1 and 2 includes a chassis 102 and a ring-like elastic belt 104. As discussed below in more detail, a first elastic belt 106 and a second elastic belt 108 are connected together to form the ring-like elastic belt 104.

With continued reference to FIG. 2, the chassis 102 includes a first waist region 116, a second waist region 118, and a crotch region 119 disposed intermediate the first and second waist regions. The first waist region 116 may be configured as a front waist region, and the second waist region 118 may be configured as back waist region. In some embodiments, the length of each of the front waist region, back waist region, and crotch region 120 may be ⅓ of the length of the absorbent article 100. The diaper 100 may also include a laterally extending front waist edge 121 in the front waist region 116 and a longitudinally opposing and laterally extending back waist edge 122 in the back waist region 118. To provide a frame of reference for the present discussion, the diaper 100 and chassis 102 of FIG. 2 is shown with a longitudinal axis 124 and a lateral axis 126. In some embodiments, the longitudinal axis 124 may extend through the front waist edge 121 and through the back waist edge 122. And the lateral axis 126 may extend through a first longitudinal or right side edge 128 and through a midpoint of a second longitudinal or left side edge 130 of the chassis 102.

As shown in FIGS. 1 and 2, the diaper pant 100 may include an inner, body facing surface 132, and an outer, garment facing surface 134. The chassis 102 may include a backsheet 136 and a topsheet 138. The chassis 102 may also include an absorbent assembly 140 including an absorbent core 142 that may be disposed between a portion of the topsheet 138 and the backsheet 136. As discussed in more detail below, the diaper 100 may also include other features, such as leg elastics and/or leg cuffs to enhance the fit around the legs of the wearer.

As shown in FIG. 2, the periphery of the chassis 102 may be defined by the first longitudinal side edge 128, a second longitudinal side edge 130; a first laterally extending end edge 144 disposed in the first waist region 116; and a second laterally extending end edge 146 disposed in the second waist region 118. Both side edges 128 and 130 extend longitudinally between the first end edge 144 and the second end edge 146. As shown in FIG. 2, the laterally extending end edges 144 and 146 are located longitudinally inward from the laterally extending front waist edge 121 in the front waist region 116 and the laterally extending back waist edge 122 in the back waist region 118. When the diaper pant 100 is worn on the lower torso of a wearer, the front waist edge 121 and the back waist edge 122 of the chassis 102 may encircle a portion of the waist of the wearer. At the same time, the chassis side edges 128 and 130 may encircle at least a portion of the legs of the wearer. And the crotch region 120 may be generally positioned between the legs of the wearer with the absorbent core 142 extending from the front waist region 116 through the crotch region 120 to the back waist region 118.

It is also to be appreciated that a portion or the whole of the diaper 100 may also be made laterally extensible. The additional extensibility may help allow the diaper 100 to conform to the body of a wearer during movement by the wearer. The additional extensibility may also help, for example, allow the user of the diaper 100 including a chassis 102 having a particular size before extension to extend the front waist region 116, the back waist region 118, or both waist regions of the diaper 100 and/or chassis 102 to provide additional body coverage for wearers of differing size, i.e., to tailor the diaper to an individual wearer. Such extension of the waist region or regions may give the absorbent article a generally hourglass shape, so long as the crotch region is extended to a relatively lesser degree than the waist region or regions, and may impart a tailored appearance to the article when it is worn.

As previously mentioned, the diaper pant 100 may include a backsheet 136. The backsheet 136 may also define the outer surface 134 of the chassis 102. The backsheet 136 may be impervious to fluids (e.g., menses, urine, and/or runny feces) and may be manufactured from a thin plastic film, although other flexible liquid impervious materials may also be used. The backsheet 136 may prevent the exudates absorbed and contained in the absorbent core from wetting articles which contact the diaper 100, such as bedsheets, pajamas, and undergarments. The backsheet 136 may also include a woven or nonwoven material, polymeric films such as thermoplastic films of polyethylene or polypropylene, and/or a multi-layer or composite materials comprising a film and a nonwoven material (e.g., having an inner film layer and an outer nonwoven layer). The backsheet may also include an elastomeric film. An example backsheet 136 may be a polyethylene film having a thickness of from about 0.012 mm (0.5 mils) to about 0.051 mm (2.0 mils). Exemplary polyethylene films are manufactured by Clopay Corporation of Cincinnati, Ohio, under the designation BR-120 and BR-121 and by Tredegar Film Products of Terre Haute, Ind., under the designation XP-39385. The backsheet 136 may also be embossed and/or matte-finished to provide a more clothlike appearance. Further, the backsheet 136 may permit vapors to escape from the absorbent core (i.e., the backsheet is breathable) while still preventing exudates from passing through the backsheet 136. The size of the backsheet 136 may be dictated by the size of the absorbent core 142 and/or particular configuration or size of the diaper 100.

Also described above, the diaper pant 100 may include a topsheet 138. The topsheet 138 may also define all or part of the inner surface 132 of the chassis 102. The topsheet 138 may be compliant, soft feeling, and non-irritating to the wearer's skin. It may be elastically stretchable in one or two directions. Further, the topsheet 138 may be liquid pervious, permitting liquids (e.g., menses, urine, and/or runny feces) to penetrate through its thickness. A topsheet 138 may be manufactured from a wide range of materials such as woven and nonwoven materials; apertured or hydroformed thermoplastic films; apertured nonwovens, porous foams; reticulated foams; reticulated thermoplastic films; and thermoplastic scrims. Woven and nonwoven materials may comprise natural fibers such as wood or cotton fibers; synthetic fibers such as polyester, polypropylene, or polyethylene fibers; or combinations thereof. If the topsheet 138 includes fibers, the fibers may be spunbond, carded, wet-laid, meltblown, hydroentangled, or otherwise processed as is known in the art.

Topsheets 138 may be selected from high loft nonwoven topsheets, apertured film topsheets and apertured nonwoven topsheets. Apertured film topsheets may be pervious to bodily exudates, yet substantially non-absorbent, and have a reduced tendency to allow fluids to pass back through and rewet the wearer's skin. Exemplary apertured films may include those described in U.S. Pat. Nos. 5,628,097; 5,916,661; 6,545,197; and 6,107,539.

As mentioned above, the diaper pant 100 may also include an absorbent assembly 140 that is joined to the chassis 102. As shown in FIG. 2, the absorbent assembly 140 may have a laterally extending front edge 148 in the front waist region 116 and may have a longitudinally opposing and laterally extending back edge 150 in the back waist region 118. The absorbent assembly may have a longitudinally extending right side edge 152 and may have a laterally opposing and longitudinally extending left side edge 154, both absorbent assembly side edges 152 and 154 may extend longitudinally between the front edge 148 and the back edge 150. The absorbent assembly 140 may additionally include one or more absorbent cores 142 or absorbent core layers. The absorbent core 142 may be at least partially disposed between the topsheet 138 and the backsheet 136 and may be formed in various sizes and shapes that are compatible with the diaper. Exemplary absorbent structures for use as the absorbent core of the present disclosure are described in U.S. Pat. Nos. 4,610,678; 4,673,402; 4,888,231; and 4,834,735.

Some absorbent core embodiments may comprise fluid storage cores that contain reduced amounts of cellulosic airfelt material. For instance, such cores may comprise less than about 40%, 30%, 20%, 10%, 5%, or even 1% of cellulosic airfelt material. Such a core may comprises primarily absorbent gelling material in amounts of at least about 60%, 70%, 80%, 85%, 90%, 95%, or even about 100%, where the remainder of the core comprises a microfiber glue (if applicable). Such cores, microfiber glues, and absorbent gelling materials are described in U.S. Pat. Nos. 5,599,335; 5,562,646; 5,669,894; and 6,790,798 as well as U.S. Patent Publication Nos. 2004/0158212 and 2004/0097895.

The diaper 100 may also include elasticized leg cuffs 156. It is to be appreciated that the leg cuffs 156 can be and are sometimes also referred to as leg bands, side flaps, barrier cuffs, elastic cuffs or gasketing cuffs. The elasticized leg cuffs 156 may be configured in various ways to help reduce the leakage of body exudates in the leg regions. Example leg cuffs 156 may include those described in U.S. Pat. Nos. 3,860,003; 4,909,803; 4,695,278; 4,795,454; 4,704,115; 4,909,803; U.S. Patent Publication No. 2009/0312730A1; and U.S. Patent Publication No. 2013/0255865A1.

As mentioned above, diaper pants may be manufactured with a ring-like elastic belt 104 and provided to consumers in a configuration wherein the front waist region 116 and the back waist region 118 are connected to each other as packaged, prior to being applied to the wearer. As such, diaper pants may have a continuous perimeter waist opening 110 and continuous perimeter leg openings 112 such as shown in FIG. 1. As previously mentioned, the ring-like elastic belt 104 is defined by a first elastic belt 106 connected with a second elastic belt 108. As shown in FIG. 2, the first elastic belt 106 defines first and second opposing end regions 106a, 106b and a central region 106c, and the second elastic 108 belt defines first and second opposing end regions 108a, 108b and a central region 108c.

The central region 106c of the first elastic belt is connected with the first waist region 116 of the chassis 102, and the central region 108c of the second elastic belt 108 is connected with the second waist region 118 of the chassis 102. As shown in FIG. 1, the first end region 106a of the first elastic belt 106 is connected with the first end region 108a of the second elastic belt 108 at first side seam 178, and the second end region 106b of the first elastic belt 106 is connected with the second end region 108b of the second elastic belt 108 at second side seam 180 to define the ring-like elastic belt 104 as well as the waist opening 110 and leg openings 112.

As shown in FIGS. 2, 3A, and 3B, the first elastic belt 106 also defines an outer lateral edge 107a and an inner lateral edge 107b, and the second elastic belt 108 defines an outer lateral edge 109a and an inner lateral edge 109b. The outer lateral edges 107a, 109a may also define the front waist edge 121 and the laterally extending back waist edge 122. The first elastic belt and the second elastic belt may also each include an outer, garment facing layer 162 and an inner, wearer facing layer 164. It is to be appreciated that the first elastic belt 106 and the second elastic belt 108 may comprise the same materials and/or may have the same structure. In some embodiments, the first elastic belt 106 and the second elastic belt may comprise different materials and/or may have different structures. It should also be appreciated that the first elastic belt 106 and the second elastic belt 108 may be constructed from various materials. For example, the first and second belts may be manufactured from materials such as plastic films; apertured plastic films; woven or nonwoven webs of natural materials (e.g., wood or cotton fibers), synthetic fibers (e.g., polyolefins, polyamides, polyester, polyethylene, or polypropylene fibers) or a combination of natural and/or synthetic fibers; or coated woven or nonwoven webs. In some embodiments, the first and second elastic belts may include a nonwoven web of synthetic fibers, and may include a stretchable nonwoven. In other embodiments, the first and second elastic belts may include an inner hydrophobic, non-stretchable nonwoven material and an outer hydrophobic, non-stretchable nonwoven material.

The first and second elastic belts 106, 108 may also each include belt elastic material interposed between the outer layer 162 and the inner layer 164. The belt elastic material may include one or more elastic elements such as strands, ribbons, or panels extending along the lengths of the elastic belts. As shown in FIGS. 2, 3A, and 3B, the belt elastic material may include a plurality of elastic strands 168 that may be referred to herein as outer, waist elastics 170 and inner, waist elastics 172.

As shown in FIG. 2, the outer, waist elastics 170 extend continuously laterally between the first and second opposing end regions 106a, 106b and across the central region 106c of the first elastic belt 106 and between the first and second opposing end regions 108a, 108b and across the central region 108c of the second elastic belt 108. In some embodiments, some elastic strands 168 may be configured with discontinuities in areas. For example, as shown in FIG. 2, the inner, waist elastics 172 extend intermittently along the first and second elastic belts 106, 108. More particularly, the inner, waist elastics 172 extend along the first and second opposing end regions 106a, 106b and partially across the central region 106c of the first elastic belt 106. The inner, waist elastics 172 also extend along the first and second opposing end regions 108a, 108b and partially across the central region 108c of the second elastic belt 108. As such, the inner, waist elastics 172 do not extend across the entirety of the central regions 106c, 108c of the first and second elastic belts 106, 108. Thus, some elastic strands 168 may not extend continuously through regions of the first and second elastic belts 106, 108 where the first and second elastic belts 106, 108 overlap the absorbent assembly 140. In some embodiments, some elastic strands 168 may partially extend into regions of the first and second elastic belts 106, 108 where the first and second elastic belts 106, 108 overlap the absorbent assembly 140. In some embodiments, some elastic strands 168 may not extend into any region of the first and second elastic belts 106, 108 where the first and second elastic belts 106, 108 overlap the absorbent assembly 140. It is to be appreciated that the first and/or second elastic belts 106, 108 may be configured with various configurations of discontinuities in the outer, waist elastics 170 and/or the inner, waist elastic elastics 172.

In some embodiments, the elastic strands 168 may be disposed at a constant interval in the longitudinal direction. In other embodiments, the elastic strands 168 may be disposed at different intervals in the longitudinal direction. As discussed in more detail below, the belt elastic strands 168, in a stretched condition, may be interposed and joined between the uncontracted outer layer and the uncontracted inner layer. When the belt elastic material is relaxed, the belt elastic material returns to an unstretched condition and contracts the outer layer and the inner layer. The belt elastic material may provide a desired variation of contraction force in the area of the ring-like elastic belt. It is to be appreciated that the chassis 102 and elastic belts 106, 108 may be configured in different ways other than as depicted in FIG. 2.

As previously mentioned, the apparatuses and methods according to the present disclosure may be utilized to assemble discrete absorbent articles 100 and/or various components of absorbent articles 100, such as for example, chassis 102, elastic belts 106, 108, and/or leg cuffs 156. Although the following methods may be provided in the context of the diaper 100 shown in FIGS. 1 and 2, it is to be appreciated that the methods and apparatuses herein may be used with various process configurations and/or absorbent articles, such as for example, disclosed in U.S. Pat. No. 7,569,039; U.S. Patent Publication Nos. US2005/0107764A1, US2012/0061016A1, and US2012/0061015A1; 2013/0255861A1; 2013/0255862A1; 2013/0255863A1; 2013/0255864A1; and 2013/0255865A1, all of which are incorporated by reference herein.

The apparatuses and methods according to the present disclosure may be utilized to supply material to assemble elastic laminates that may be used in various components of absorbent articles, such as for example, elastic belts 106, 108 and/or leg cuffs 156. Such elastic laminates may be assembled by positioning the supplied material between two or more substrate layers. It is to be appreciated that the elastic laminates may be constructed in various ways, such as for example, in accordance with the methods and apparatuses disclosed in U.S. Pat. No. 8,440,043 and U.S. Patent Publication Nos. US2013/0255861A1; US2013/0255862A1; US2013/0255863A1; US2013/0255864A1; and US2013/0255865A1, which are all incorporated by reference herein. Although the following methods may be provided in the context of the diaper 100 shown in FIGS. 1 and 2, it is to be appreciated that elastic laminates can be used with various embodiments of diapers manufactured according the methods disclosed herein, such as for example, the absorbent articles disclosed in U.S. Pat. No. 7,569,039, filed on Nov. 10, 2004; U.S. Patent Publication No. 2005/0107764A1, filed on Nov. 10, 2004; U.S. patent application Ser. No. 13/221,127, filed on Aug. 30, 2011; and U.S. patent application Ser. No. 13/221,104, filed on Aug. 30, 2011, which are all hereby incorporated by reference herein.

Figure 4:
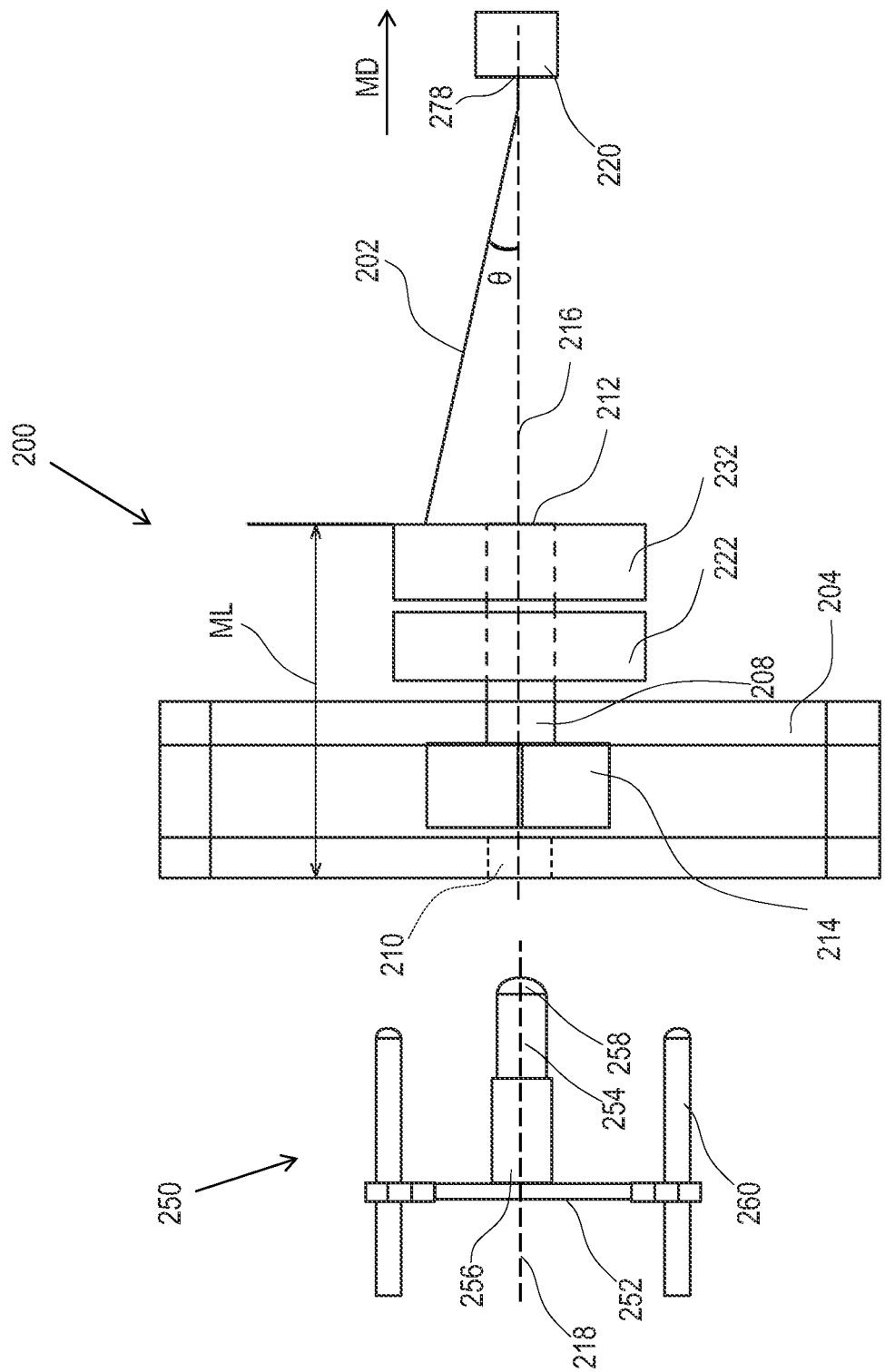
FIG. 4 is a top view of an unwind apparatus and a loading apparatus in accordance with one non-limiting embodiment of the present disclosure.

FIG. 4 shows an embodiment of the unwind apparatus 200 that may be used to load and/or unwind materials used in the manufacture of an absorbent article 100. As shown, the unwind apparatus may include a mandrel 208. The mandrel 208 may include a proximal end portion 210 and a distal end portion 212, opposite the proximal end portion 210, and a central longitudinal mandrel axis 216. The mandrel 208 may also have a mandrel length ML, which may be long enough to support at least two spools, as shown in FIG. 4. In an example embodiment, the mandrel length ML may be from about 3 inches to about 20 inches. A portion of the mandrel 208 may be supported by a mandrel support member 214. The mandrel support member 214 may be associated with the mandrel 208. The movement of the mandrel support member 214 with respect to the mandrel 208 is explained in more detail below. The mandrel 208 may be adapted to support a spool 222, 232. The spool 222, 232 may include a core 224, 234 and a strand of material 226, 236 wound about the core. The spool 222, 232 generally surrounds the central longitudinal mandrel axis 216, which may be substantially parallel to the machine direction MD. More specifically, the core of the spool 222, 232 may surround the outside surface of the mandrel 208.

Generally, the material 226, 236 wound about the core 224, 234 of the spool 222, 232 may be unwound and fed into a control device 220. The control device 220 may be used to regulate the unwind speed, the tension on the material being unwound, and other variables affecting the supply of the material to the manufacturing line. Example control devices are disclosed in U.S. Pat. No. 7,878,447, filed on Nov. 25, 2009 and U.S. Pat. No. 7,905,446, filed on Dec. 29, 2006, which are all hereby incorporated by reference herein.

The control device 220 may be located such that the entry point 278 of the material 226, 236 into the control device 220 is in line with the central longitudinal mandrel axis 216. Thus, the material 226, 236 may be unwound at an unwind angle $\theta$ to the central longitudinal mandrel axis 216. In one example embodiment, the unwind angle $\theta$ may be from about 5 degrees to about 25 degrees. It is to be appreciated that the angle $\theta$ is based on the radius of the spool. The maximum unwind angle $\theta$ may occur when the spool first begins to unwind and the material is located farthest away from the central longitudinal mandrel axis 216. The minimum unwind angle $\theta$ may occur just before the spool is empty and/or the material being unwound is in contact with the core.

The loading apparatus 250 may be configured to support a replacement spool 242 of material 246. To support the spool and removably engage with the unwind apparatus, the loading apparatus 250 may include a base member 252 and a loading shaft 254. The loading shaft 254 may include a proximal end portion 256 and a distal end portion 258, opposite the proximal end portion 256, and a central longitudinal shaft axis 218. The proximal end portion 256 of the loading shaft 254 may be connected with the base member 252. The distal end portion 258 of the loading shaft 254 may be releasably connectable with the proximal end portion 210 of the mandrel 208. The replacement spool 242 may substantially surround the central longitudinal shaft axis 218 and be moveable between the proximal end portion 256 and the distal end portion 258 of the loading shaft 254. Stated another way, the replacement spool 242 may include a core 244. The core 244 may be moveable between the proximal end portion 256 and the distal end portion 258 of the loading shaft 254.

In some embodiments, additional support of the loading apparatus 250 may be needed. For example, in certain instances the loading apparatus 250 holding the replacement spool 242 may be too heavy for an operator to support by himself or herself. Thus, in some embodiments, the loading apparatus 250 may also include a dowel member 260, which may extend from the base member 252. The dowel member 260 may be configured to engage an aperture 206 defined by the frame 204 of the unwind apparatus 200. It is to be appreciated that the unwind apparatus 200 may include a dowel member 260 and the base member 252 may define an aperture 206.

Thus, the dowel member 260 may extend from the frame 204 and the aperture 206 may be configured to receive the dowel member 206 (not shown). Further, the unwind apparatus 200 may include a dowel member 260 extending from the frame 206 and the frame 206 may also define an aperture 206. Similarly, the loading apparatus 250 may include a base member 252 defining an aperture 206 and include a dowel member 260 extending from the base member 252 (not shown). The dowel member 260 received by the aperture 206 may provide additional support of the loading apparatus 250 while the replacement spool 242 is moved from the loading apparatus 250 to the unwind apparatus 200. It is to be appreciated that any number of dowel members and any number of corresponding apertures may be used to provide additional support to the loading apparatus. For example, a single dowel member and a corresponding single aperture may be used in some embodiments. It is also to be appreciated that in some embodiments, where additional support of the loading apparatus is not needed, the unwind apparatus may not include a dowel member and a corresponding aperture.

As previously mentioned, the unwind apparatus and the loading apparatus may be reconfigurable. For example, in a first configuration, the loading shaft 250 may be associated with the unwind apparatus 200 such that a spool may be moved from the loading apparatus to the unwind apparatus and vice versa. More specifically, the distal end portion 258 of the loading shaft 254 may be associated with the proximal end portion 210 of the mandrel 208. Further, the base member 252 may be associated with the frame 204. The mandrel support member 214 may be disassociated from the mandrel 208 such that the replacement spool is moveable along the loading shaft 254 and onto to the mandrel 208. In a second configuration, the unwind apparatus may be disassociated with the loading apparatus. More specifically, the distal end portion 258 of the loading shaft 254 may be disassociated with the proximal end portion 210 of the mandrel 208, and the base member 252 may be disassociated with the frame 204. Further, the mandrel support member 214 may be associated with the mandrel 208. Each of these configurations will be better understood in view of the following disclosure.

Figure 5:
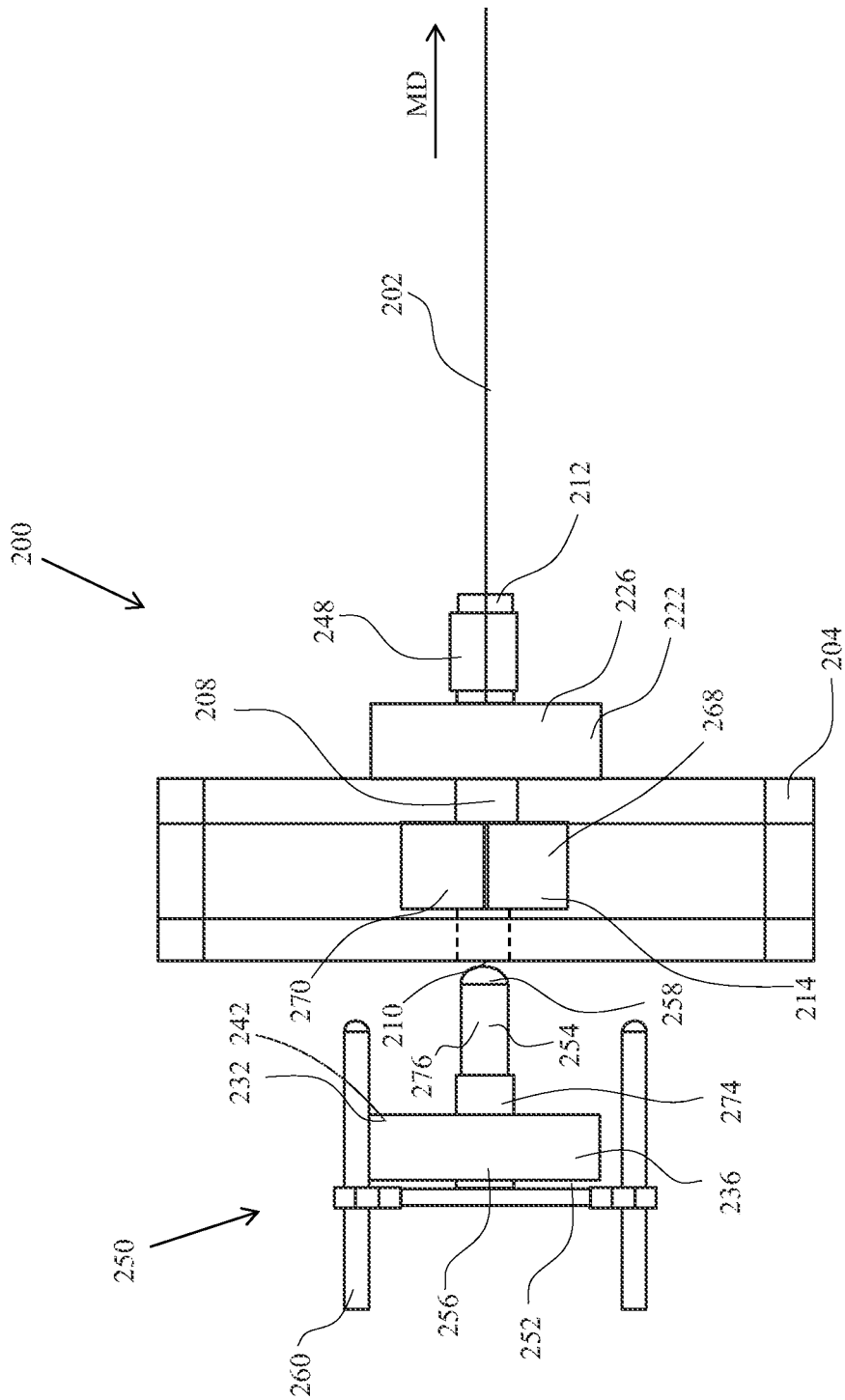
FIG. 5 is a top view of an unwind apparatus and a loading apparatus in accordance with one non-limiting embodiment of the present disclosure.
Figure 11:
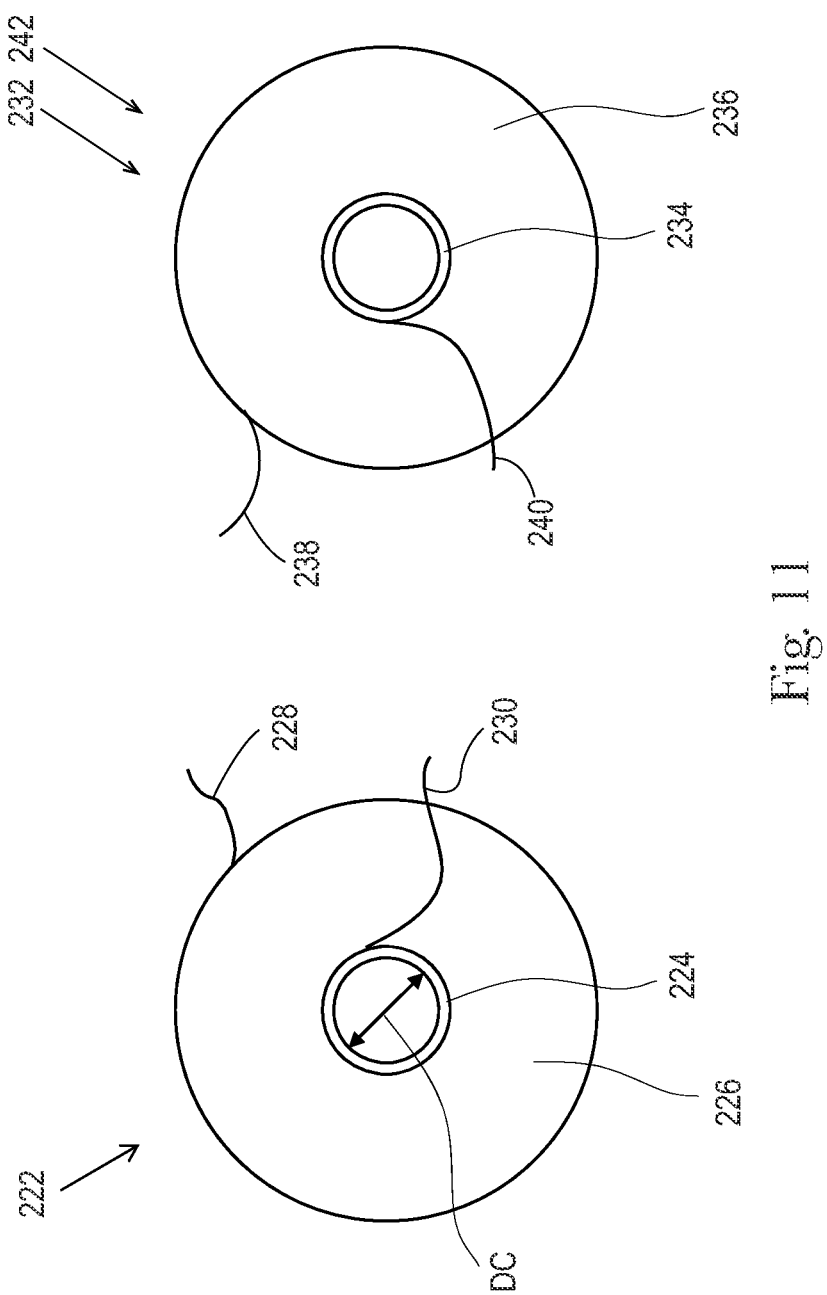
FIG. 11 is a schematic representation of a first spool and a second spool in accordance with one non-limiting embodiment of the present disclosure.

Referring to FIGS. 5 and 6, the unwind apparatus 200 may provide material 202 to manufacture absorbent articles 100. Depending on manufacturing speeds, spool size, and supply demands, spools of material may need to be replaced relatively frequently in order to create an uninterrupted supply of material to the manufacturing line. As shown in FIGS. 5 and 6, when a spool has been depleted, such that only the core of the spool remains, the empty spool 248 may be disposed on the distal end portion 212 of the mandrel 208. Adjacent to the empty spool 248 may be a first spool 222. The first spool 222 may include a first core 224 and a first stand of elastic material 226 wound around the core 224, as shown in FIG. 11. The spool that supplies the manufacturing line is also referred to herein as the active spool. The first spool 222 may become the active spool at the time the empty spool 248 no longer supplies the manufacturing line.

As the strand of elastic material 226 is unwound, the mandrel 208 supports the first spool 222. The mandrel 208 may be a substantially rigid member that extends away from the frame 204, toward the unwind direction of the strand of elastic material 202. In some embodiments, the diameter of the mandrel 208 may be sized to allow the spool to rotate or not rotate about the surface of the mandrel 208. The diameter of the mandrel 208 may be less than the core diameter DC, as shown in FIG. 11. The core diameter DC may be from about 20 mm to about 225 mm and/or from about 50 mm to about 200 mm and/or from about 75 mm to about 150 mm, including all 0.01 mm increments therebetween. For example, in some embodiments, the mandrel 208 may include a diameter of from about 20 mm to about 225 mm and/or from about 24 mm to about 199 mm and/or from about 74 mm to about 154 mm, including all 0.01 mm increments therebetween. In some example embodiments, the core 224, 234 of the spool 222, 232 may not rotate about the mandrel 208. The mandrel 208 may be sized such that the core 224, 234 fits snugly against the exterior of the mandrel 208. This allows the core 224, 234 to slid axially along the length of the mandrel 208 but inhibits rotation of the core 224, 234 about the central longitudinal mandrel axis 216.

In some embodiments, the mandrel may rotate about a longitudinal mandrel axis. Thus, the diameter of the mandrel 208 may be sized to control rotation of the spool. Stated differently, the spool may rotate with the rotation of the mandrel 208 about the longitudinal mandrel axis 216.

The mandrel 208 may be supported by a mandrel support member 214. The mandrel support member 214 may be associated with the mandrel 208 to allow spools to be loaded and/or unloaded from the mandrel 208. Further, the mandrel support member 214 may be moveably connected with the frame 204 of the unwind apparatus 200. The mandrel support member 214 may include a first block member 268 and a second block member 270. The mandrel support member 214 may be any device that provides adequate support for the mandrel 208. For example, in some embodiments, the mandrel support member 214 may also include one or more arms.

Still referring to FIGS. 5 and 6, the empty spool 248, which includes a core without a strand of material, and the activation of the first spool 222 may signal to the operator that a second spool 232 may be loaded onto the unwind apparatus 200. The loading apparatus 250 may be used to load a second spool 232 onto the unwind apparatus 200. The loading apparatus 250 may include a loading shaft 254 and a base member 252. The loading shaft 254 may include a proximal end portion 256 connected with the base member 252 and a distal end portion 258 opposite from the base member 252. The loading shaft 254 may be adapted to receive the second spool 232. The second spool 232 may include a core 244 (not shown) and a second stand of elastic material 236 wound around the core 244. The second spool 232 is also referred to herein as a replacement spool 242. The core 244 of the second spool 232 may be moveable along the length of the loading shaft 254.

The loading shaft 254 may include a first circumference 274 and a second circumference 276. The first circumference 274 may be greater than, less than, or equal to the second circumference 276. The first circumference 274 and the second circumference 276 may be equal to, greater than, or less than the circumference of the mandrel 208. In one example embodiment, the second circumference 276 may be less than or greater than the circumference of the mandrel 208. The loading shaft 254 may include a second circumference 274 such that the shaft may be sized to substantially surround the external surface of the mandrel 208 or, in another example embodiment, to fit within the internal surface of the mandrel 208. In either configuration, the second circumference 276 may allow the loading shaft 254 to engage with and support the mandrel 208 during loading of the replacement spool 242.

For example, in some embodiments, the loading shaft 254 may include a first circumference 274 and a second circumference 276. The first circumference 274 may be greater than the second circumference 276, as shown in FIG. 5. The portion of the loading shaft 254 having the second circumference 276 may be less than the circumference of the inner surface of the mandrel 208. Thus, the loading shaft 254 having the second circumference 276 may slidably engage with the mandrel 208. The loading shaft 254 may slide into the interior of the mandrel 208 up to the portion of the loading shaft 254 having the first circumference 274, which may be greater than the interior surface circumference of the mandrel 208.

In some embodiments, the loading apparatus 250 may also include a dowel member 260. The dowel member 260 may extend from the base member 252 in a direction substantially parallel to the loading shaft 254. In other embodiments, the dowel member 260 may also extend through the base member 252. Generally, the dowel member 260 may be configured to be received by an aperture 206 defined by the frame 204. It is to be appreciated that the fame 204 may include a dowel member and the base member 252 may define an aperture (not shown). Thus, the aperture within the base member may be configured to receive the dowel member extending from and/or through the frame. It is to be appreciated that any number of dowel members and any number of corresponding apertures may be used to adequately support the loading apparatus. For example, two dowel members and two corresponding apertures may be used in some embodiments.

Referring now to FIG. 7, the unwind apparatus 200 may be engaged with the loading apparatus 250 to load a replacement spool 242. More specifically, the base member 252 of the loading apparatus 250 may associate with the frame 204 of the unwind apparatus 250. Additionally, the loading apparatus 250 may engage the unwind apparatus 200 such that the distal end portion 258 of the loading shaft 254 may be slidably engaged with an interior surface or exterior surface of the mandrel 208. In one example embodiment, the distal end portion 258 may enter the interior of the mandrel 208 at the proximal end portion 210 of the mandrel 208. The distal end portion 258 of loading shaft 254 may slide along the interior surface of the mandrel 208 until the loading apparatus 250 is in position for the replacement spool 242 to be moved onto the mandrel 208. In some embodiments, the distal end portion 258 of the loading shaft 254 may substantially surround an exterior surface of the proximal end portion 210 of the mandrel 208. When the distal end portion 258 of the loading shaft 254 is associated with the proximal end portion 256 of the mandrel 208, the central longitudinal mandrel axis 216 may be substantially parallel to the central longitudinal shaft axis 218.

When the distal end portion 258 of the loading shaft 254 is associated with the proximal end portion 256 of the mandrel 208, the central longitudinal mandrel axis 216 may be substantially in line with the central longitudinal shaft axis 218. The longitudinal mandrel axis 216 may be substantially parallel to the central longitudinal shaft axis 218. In yet another embodiment, when the distal end portion 258 of the loading shaft 254 is associated with to the proximal end portion 256 of the mandrel 208, the central longitudinal mandrel axis 216 and the central longitudinal shaft axis 218 may be substantially parallel to the machine direction MD.

Further, a dowel member 260 may be attached to at least one of the base member 252 and the frame 204. The dowel member 260 may be used to provide additional stability to the loading apparatus 250 and/or the mandrel 208 during transfer of the replacement spool 242. In one example embodiment, as shown in FIG. 7, the dowel member 260 may extend through the aperture 206 defined by the frame 204.

As previously discussed, the loading shaft 254 may have a surface having a first circumference 274 greater than or equal to the exterior surface circumference of the mandrel 208. Thus, when the loading apparatus 250 engages the unwind apparatus 200 such that the loading shaft 254 slidably engages the mandrel 208, the first circumference 274 may act as a guide. More specifically, loading apparatus 250 may engage the unwind apparatus 200 up to the point where the first circumference 274 of the loading shaft 254 abuts the exterior surface circumference of the mandrel 208. The first circumference 274 of the loading shaft 254 may indicate to the manufacturing operator that the loading device 250 is in place when the loading shaft 254 abuts the exterior surface circumference of the mandrel 208. The first circumference 254 may stop the loading apparatus 250 from slidably advancing any further into the mandrel 208.

Figure 8B:
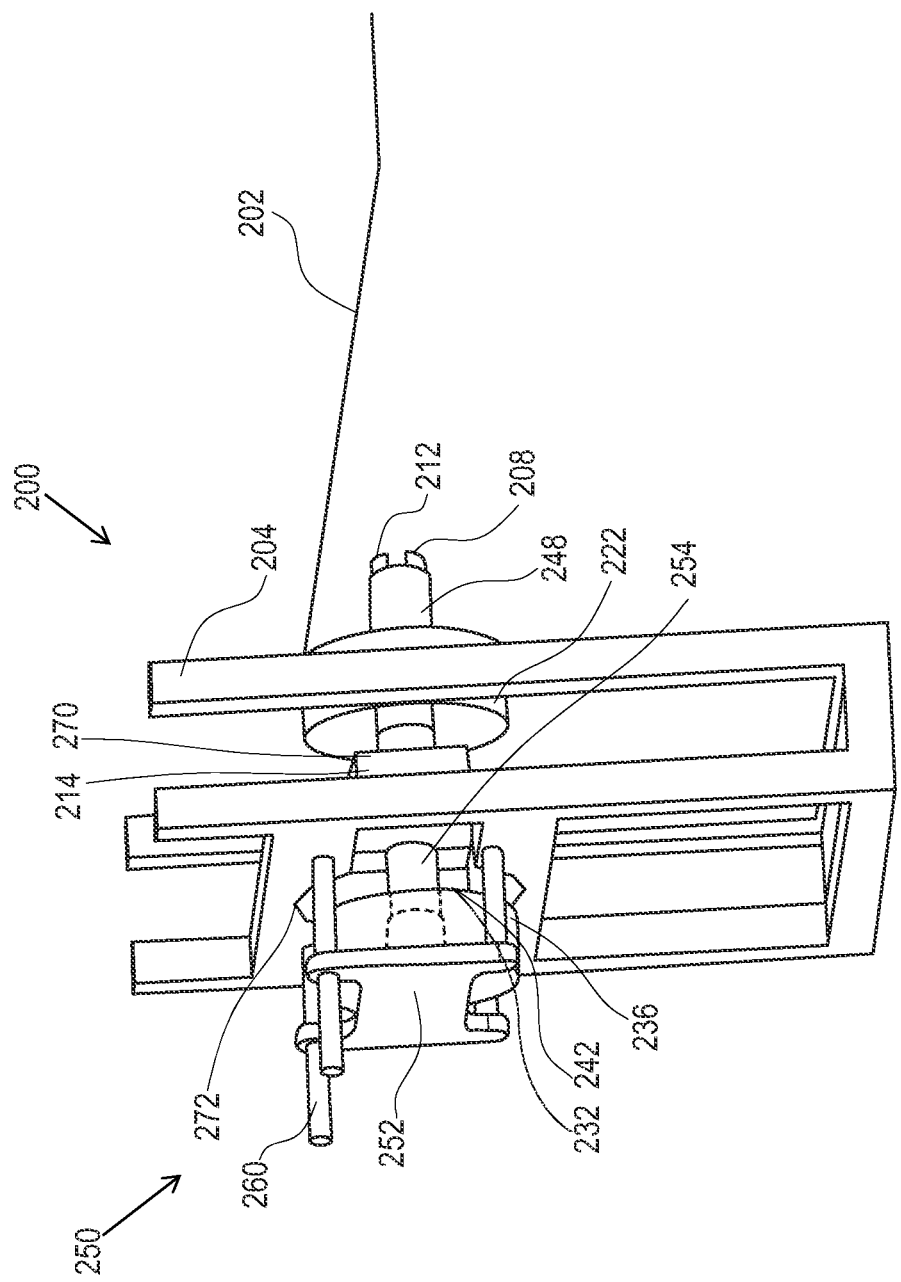
FIG. 8B is a perspective view of an unwind apparatus and a loading apparatus in accordance with one non-limiting embodiment of the present disclosure.

Referring now to FIGS. 8A and 8B, once the loading apparatus 250 has been engaged with the unwind apparatus 200 such that the distal end portion 258 of the loading shaft 254 may be associated with the proximal end portion 256 of the mandrel 208 and the mandrel 208 has sufficient support from the loading apparatus 205, the mandrel support member 214 may be disassociated from the mandrel 208. As shown in FIG. 8A, the loading apparatus 250 may support the mandrel 208 once the mandrel support member 214 has been disassociated from the mandrel 208. The mandrel support member 214 may be disassociated so that the replacement spool 242 may be moved from the loading shaft 254 to the mandrel 208.

Figure 8C:
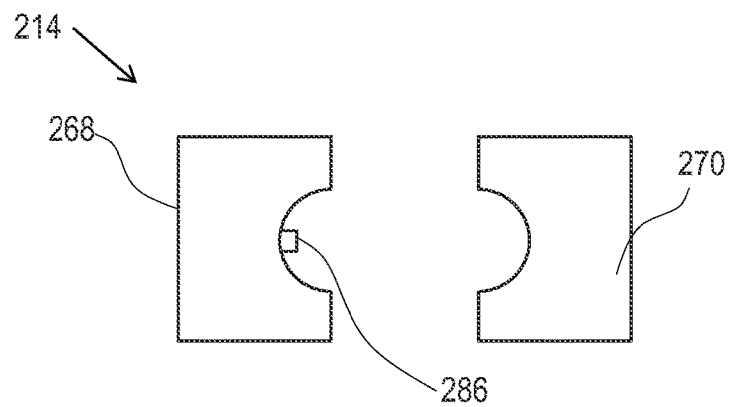
FIG. 8C is a schematic representation of a mandrel support member in accordance with one non-limiting embodiment of the present disclosure.

As shown in FIGS. 8A, 8B and 8C, the mandrel support member 214 may include a first support block member 268 and a second support block member 270. At least one of the first support block member 268 and the second support block member 270 may include a support key 286, 287 as shown in FIG. 8C. The support key 286, 287 may be connected to the support block member and/or machined in a portion of the support block member 268, 270. The support key 286 connected to the support block may correspond with a mandrel key connected to and/or machined in a portion of the exterior surface of the mandrel 208. The support key 286, 287 in combination with the mandrel key may be used to ensure proper placement and alignment of the mandrel 208 prior to engagement of the loading apparatus 250 and after transfer of a replacement spool 242 onto the mandrel 208. To release the mandrel 208, the first support block 268 and the second support block 270 may move in a direction substantially perpendicular to the central longitudinal mandrel axis 216. It is to be appreciated that the first support block 268 and the second support block 270 may move in any direction away from the mandrel 208 so as to provide sufficient space for the second spool 232 to advance from the loading apparatus 250 onto the mandrel 208.

Figure 8D:
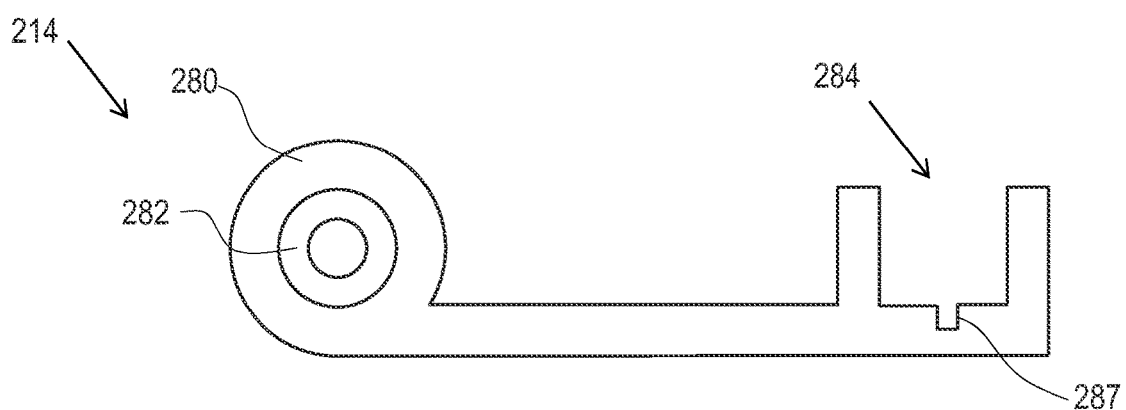
FIG. 8D is a schematic representation of a mandrel support member in accordance with one non-limiting embodiment of the present disclosure.

In some example embodiments, the mandrel support member 214 may include an arm 280, also referred to as a clamp, as shown in FIG. 8D. The arm 280 may be pivotally connected to the mandrel 208. More specifically, the arm 280 may be rotatable about an arm pin 282 that may be connected to the frame 204. The arm 280 may extend in a direction substantially perpendicular to the machine direction MD. In some embodiments, the arm pin 282 may allow the arm rotate and/or to be moveable along the length of the mandrel 208. Thus, the arm 280 may slidably engage the arm pin 282. The arm 280 may extend outward from the arm pin 282 in a direction substantially perpendicular to the arm pin and pivotally connect to any one of the distal end portion 212, the proximal end portion 210, and/or any portion along the length therebetween of the mandrel 208. In some embodiments, the arm 280 may include a holder portion 284, opposite the arm pin, that may support the mandrel 208. It is to be appreciated that the holder portion 284 may include any structure that allows for stabilization of the mandrel 208. For example, the holder portion 284 may include two upright portions, as shown in FIG. 8D, and/or a concave portion and/or convex portion and/or a single upright portion. Similar to the above, the arm 280 may also include a support key 287 that corresponds to the mandrel key to ensure the mandrel 208 maintains proper alignment and position pre and post loading of the replacement spool 242. It is to be appreciated that more than one arm may be used to support the mandrel 208.

Referring to FIG. 8B, the mandrel support member 214 may be disassociated with the mandrel 208. Further, the loading apparatus 250 may be engaged with the unwind apparatus 200. More specifically, the loading shaft 254 may be slidably engaged with the mandrel 208. The replacement spool 244 may then move along the loading shaft 254 toward the distal end portion 258 of the loading shaft. The replacement spool 244 may pass through an opening 272 in the frame 204 and onto the mandrel 208. The replacement spool 244 may be moved along the loading shaft 254 and the mandrel 208, in the machine direction MD, manually and/or mechanically. For example, an operator may manually move the spool by pushing the replacement spool 244 along the length of the loading shaft and onto the mandrel 208 with his or her hand. The operator's hand may directly interact with the spool or the operator may use a device, such as a rigid lever, to engage and slid the spool. In some example embodiments, the spool may be mechanically moved such as by a motor. More specifically, at least one of the unwind apparatus and the loading apparatus 250 may also include a motor (not shown) that may operatively engage a device to exert force on the core or any other portion of the replacement spool to move the spool from the loading shaft 254 onto the mandrel 208.

Figure 9:
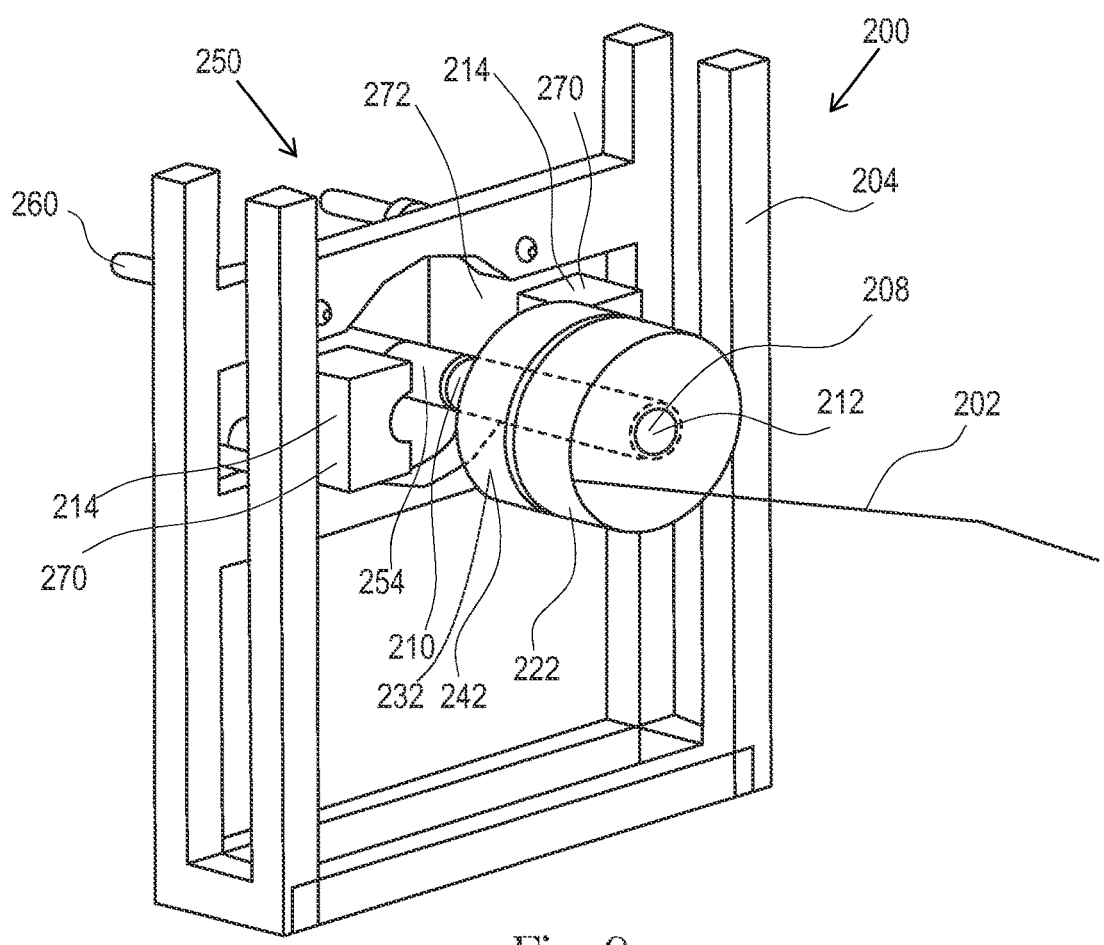
FIG. 9 is a perspective view of an unwind apparatus and a loading apparatus in accordance with one non-limiting embodiment of the present disclosure.

Referring to FIG. 9, the second spool 232, also referred to as the replacement spool 242, may be positioned adjacent to the first spool 222. In one embodiment, the second spool 232 may engage the first spool 232 and both the first spool 222 and the second spool 232 may move toward the distal end portion 212 of the mandrel 208. As the first and second spools 222, 232 advance, the first spool 222 may engage the empty spool 248, as shown in FIG. 8B. The first spool 222 may push the empty spool 248 off the distal end portion 212 of the mandrel 208. It is to be appreciated that during the loading of the replacement spool 242 and the removal of the empty spool, the manufacturing line may continuously be supplied a first strand of material by the first spool 222. Thus, the empty spool 248, which may include a core, may be configured to drop, due to the force of gravity, from the distal end portion 212 of the mandrel 208. Further, the core of the empty spool 248 may be designed such that if the core interacts with the material being unwound from the spool, the core does not interrupt the unwinding of the material and/or does not damage the material. In some embodiments, the empty spool 248 may be pushed off the distal end portion 212 of the mandrel 208 at a specific period in time. More specifically, the empty spool 248 may be pushed off the distal end portion 212 of the mandrel 208 at a period in time when the empty spool 248 will not contact the material being unwound from the spool 222. Further, in some embodiments, the empty spools 248 that have been pushed off the distal end portion 212 of the mandrel 208 may be collected in a basin or other holding container so that the empty spools 248 do not interfere with the unwind operation and/or hinder the safety of operators working around the unwind device.

Once the first spool 222 and the second spool 242 have progressed toward the distal end portion 212 of the mandrel 208, the mandrel support member 214 may re-engage the mandrel 208. As discussed above, the mandrel 208 may include a mandrel key and the mandrel support member 214 may include a support key 286, 287, as shown in FIGS. 8C and 8D. When the mandrel support member 214 engages the mandrel 208, the mandrel key may associate with the support key to ensure that the mandrel support member 214 is properly engaged with the mandrel 208, and to ensure that the mandrel 208 maintains proper position and alignment for unwinding the spools 242, 222.

Figure 10:
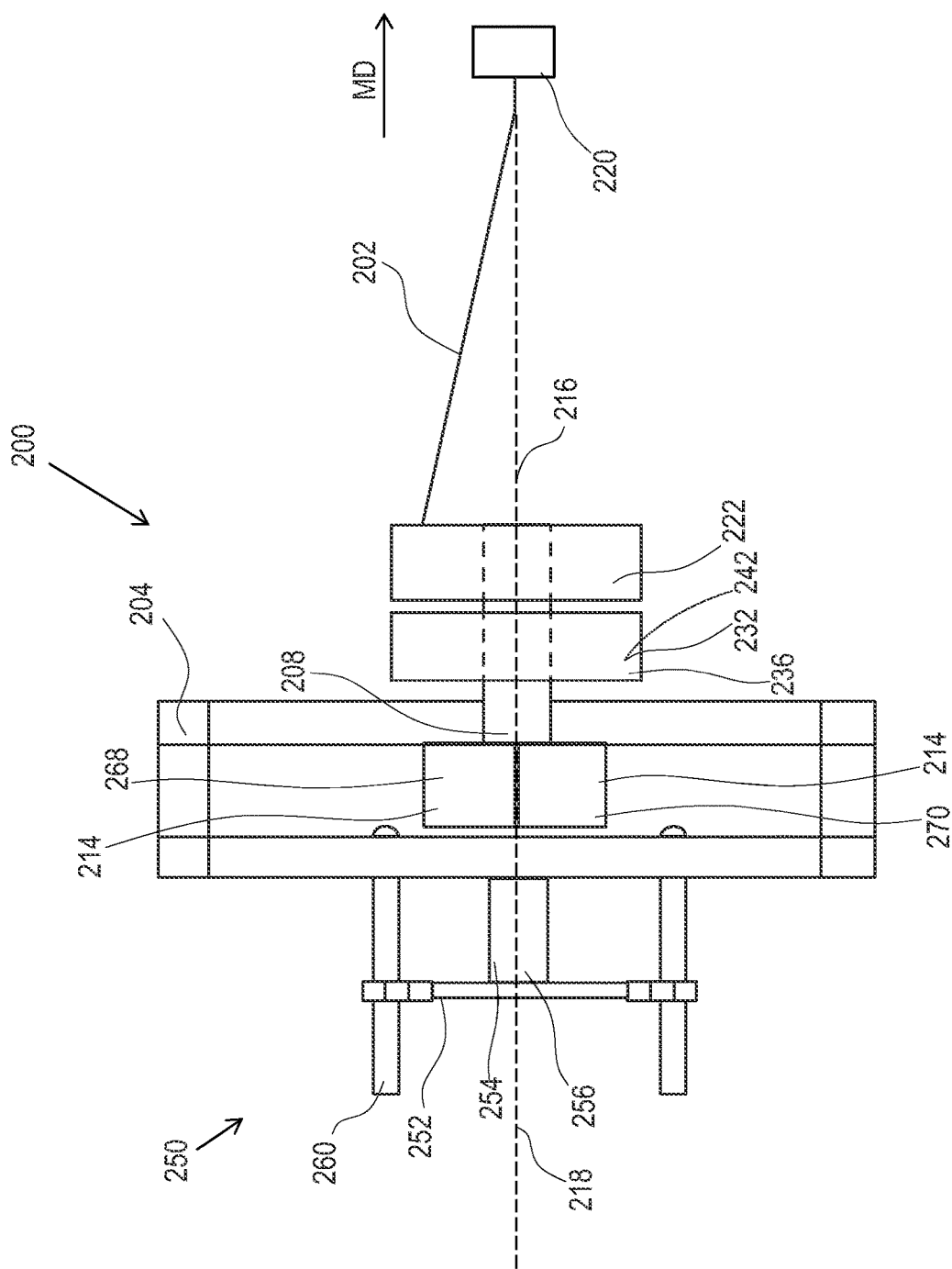
FIG. 10 is a top view of an unwind apparatus and a loading apparatus in accordance with one non-limiting embodiment of the present disclosure.

To supply a constant stream of material to the manufacturing line, the first spool 222 may be connected to the second spool 242. Referring to FIGS. 10 and 11, the first spool 222 may comprise a first core 224 and a first strand of material 226. Similarly, the second spool 232, also referred to as the replacement spool 242, may comprise a second core 234 and a second strand of material 236 wound around the second core 234. Further, the first strand of material may comprise a first end portion 228 and a second end portion 230, opposite the first end portion 228. More specifically, the second end portion 230 of the first strand of material 226 may be adjacent to the first core 224 of the first spool 222. Similarly, the second strand of material 236 may comprise a first end portion 238 and a second end portion 240. The second end portion 240 of the second strand of material 236 may be adjacent to the second core 234 of the second spool 232. Thus, during operation, the first end portion 228 of the first strand of material 226 may be unwound and passed through the control device 220. Further, the second end portion 230 of the first strand of material 226 may be attached to the first end portion 238 of the second strand of material 236 such that when the first spool 222 becomes empty the second spool 232 may immediately being to unwind providing a constant stream of material to the manufacturing line. It is to be appreciated that the second end portion 240 of the second strand of material 236 may be attached to the next replacement spool.

Figure 12:
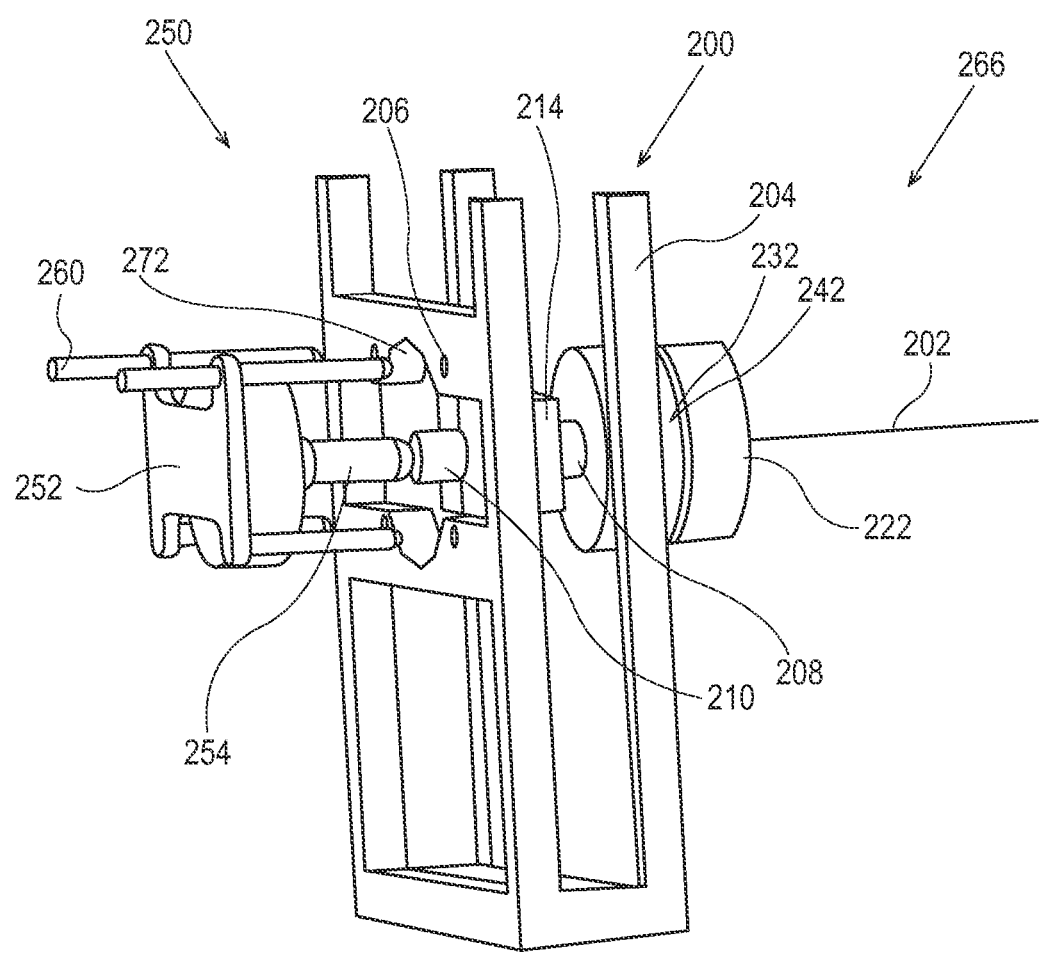
FIG. 12 is a perspective view of an unwind apparatus and a loading apparatus in accordance with one non-limiting embodiment of the present disclosure.

When the mandrel support member 214 has sufficient support of the mandrel 208, the loading apparatus 254 may be disengaged from the unwind apparatus 200, as illustrated in FIG. 12. More specifically, the dowel members 260 of the loading apparatus 250 may be removed from the apertures 206 defined by the frame 206. It is to be appreciated that the frame 206 may include dowel members 206 and the loading apparatus 250 may define the apertures 206, as previously discussed. Further, the loading shaft 254 of the loading apparatus 250 may be slid along the mandrel 208 such that the loading shaft 254 is no longer in contact with the mandrel 208.

Figure 13:
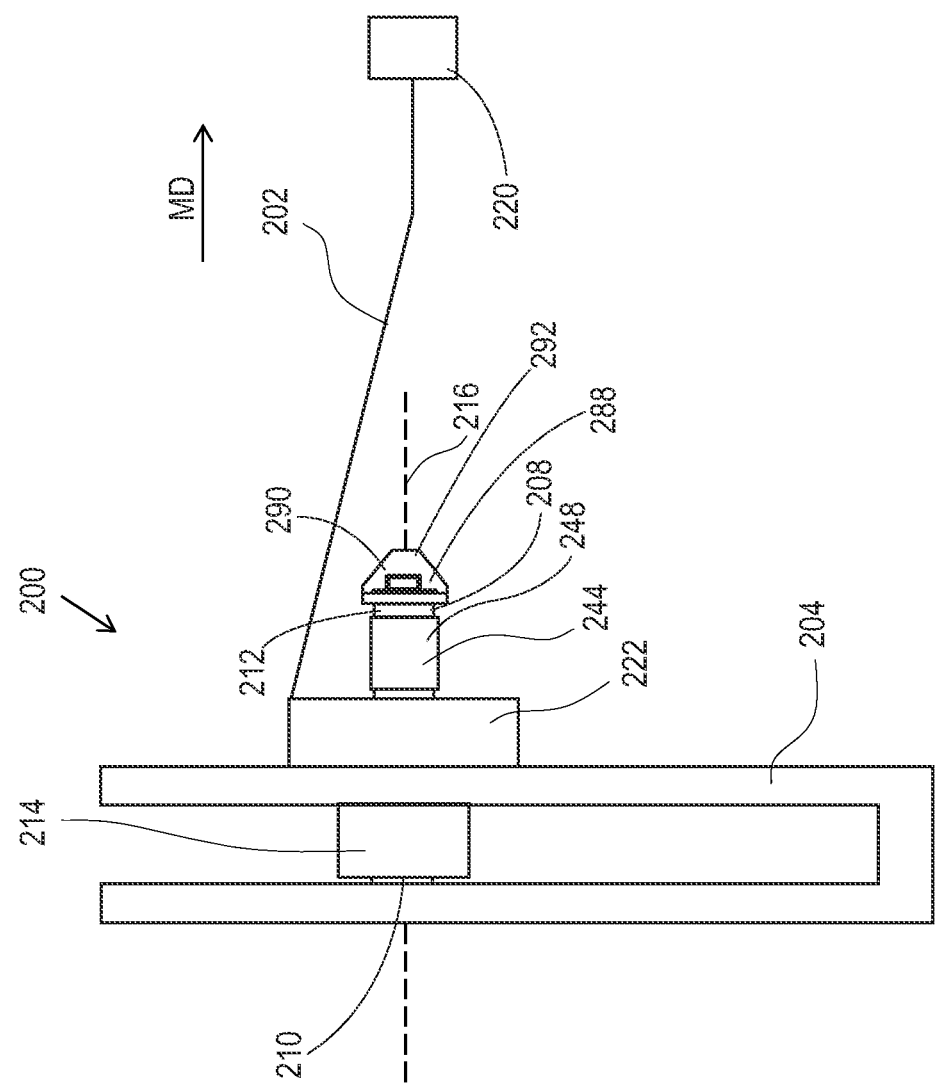
FIG. 13 is a side view of an unwind apparatus in accordance with one non-limiting embodiment of the present disclosure.
Figure 14:
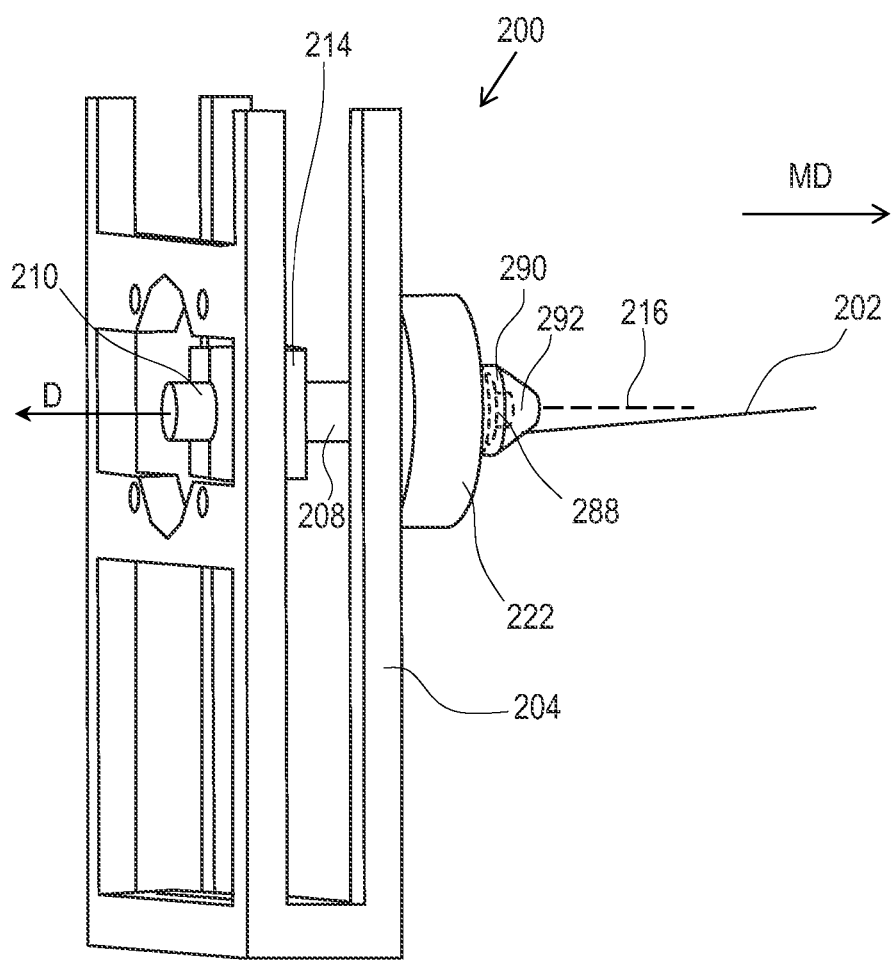
FIG. 14 is a perspective view of an unwind apparatus and a loading apparatus in accordance with one non-limiting embodiment of the present disclosure.

In some embodiments, the unwind apparatus 200 may include a removal component 290, as illustrated in FIGS. 13 and 14, configured to discard and/or remove the empty spool 248, which may include only a core 244. The removal component 290 may include a demolishing component 288 and a protective component 292. The demolishing component 288 may be adjacent to the distal end portion 212 of the mandrel 208. The demolishing component 288 may be positioned such that as the empty spool 248 is moved toward the distal end portion 212 of the mandrel 208, the demolishing component 288 may intercept the empty spool 248, which includes a core 244. The demolishing component 288 may be configured to grind the core 244 of the empty spool 248 into two or more pieces. Thus, the demolishing component 288 may include a blade or other device that may break down the empty spool 248 into several pieces. In order to capture the pieces of core, a vacuum may be fluidly connected to the mandrel 208. For example, the vacuum may be applied at the proximal end portion 210 of the mandrel 208 such that the pieces of core of the empty spool may be sucked into the interior portion of the mandrel 208. More specifically, the pieces of core may enter the interior of the mandrel 208 toward the distal end portion 212 and travel the length of the mandrel 208 toward the proximal end portion 210 of the mandrel 208 where the pieces may then be removed by the vacuum device. Arrow D, shown in FIG. 14, indicates the direction of travel of the pieces of core.

In some embodiments, the protective component 292 may substantially surround the demolishing component 288. The protective component 292 may be configured to safeguard operators working near the demolishing component 288. Further, the protective component 292 may aid in directing the pieces of core into the interior of the mandrel 208. Further still, the protective component 292 may aid in controlling any dust or debris that may be generated when the empty spool 248 is grinded by the demolishing component 288.

It is to be appreciated that the protective component 292 and the demolishing component 288 may be designed such that these components do not interfere with the unwinding of the material 226, 236 from the spool 222, 232. In some embodiments, the protective component 292 and/or the demolishing component 288 may be retractable. More specifically, the protective component 292 and/or the demolishing component 288 may retract such that the material being unwound from the spool does not contact the protective component 292 and/or the demolishing component 288 (not shown).

Figure 15:
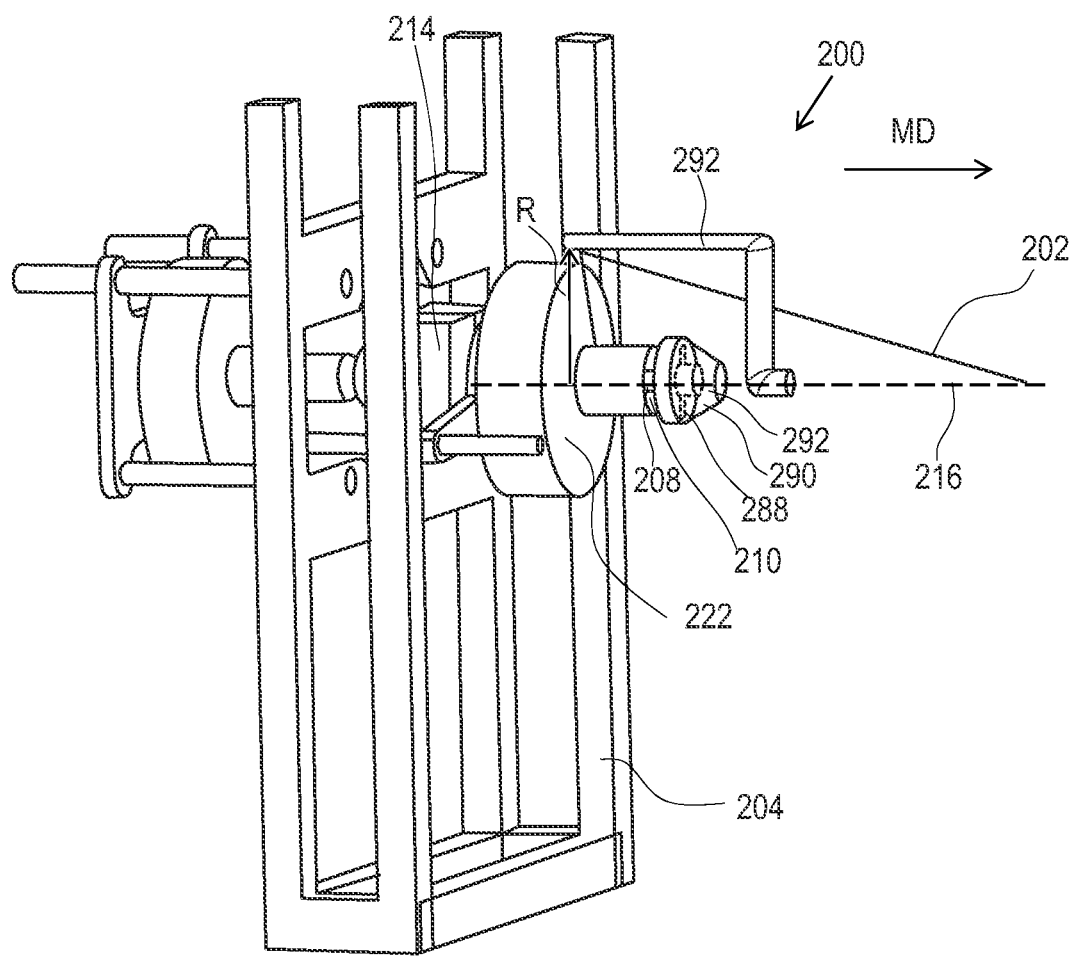
FIG. 15 is a perspective view of an unwind apparatus and a loading apparatus in accordance with one non-limiting embodiment of the present disclosure.

In some embodiments, to prevent the unwinding material from contacting the protective component 292 and the demolishing component 288, the unwind apparatus 200 may include a rotatable arm 296 adjacent the distal end portion 212 of the mandrel 208, as illustrated in FIG. 15. An exemplary rotary arm for use with the unwind apparatus of the present disclosure are described in U.S. Patent Publication Nos. US 2013/0112794 and US 2013/0112800, which are all hereby incorporated by reference herein. The rotatable arm 296 may be used to aid in the unwinding of the material 226, 236 from the spool 222, 232. More specifically, the rotatable arm 296 may allow the unwind radius R, which is the distance from the central longitudinal mandrel axis 216 to the point where the material 226, 236 leaves the spool 222, 232, to remain constant as the material is unwound from the spool. Stated another way, the rotatable arm 296 may prevent the unwind radius R from reducing to the point that the material 216 interferes with the protective component 292 and/or the demolishing component 288.

In view of the aforementioned, a method for loading elastic material on an unwinding apparatus may include the following steps. An unwind apparatus 200 may include a frame, a mandrel including a proximal end portion and a distal end portion, and a mandrel support member connected with the frame and the mandrel. A first spool may be supported on the mandrel, and the first spool may include a first core and a first strand of elastic material wound around the first core. The first strand of elastic material may be unwound from the first core in a direction past the distal end of the mandrel. A second spool may be provided that includes a second core and a second strand of elastic material wound around the second core. The second spool may be placed onto a loading shaft. The loading shaft may include a proximal end portion and a distal end portion. The loading shaft may be associated with the mandrel, and the mandrel support member may be disassociated with the mandrel. More specifically, the distal end portion of the loading shaft may be slidably engaged with the proximal end portion of the mandrel.

In some embodiments, a base member may be associated with the frame to provide additional support to the mandrel. More specifically, the base member may include a dowel member and the frame may include an aperture, or, the base member may include an aperture and the frame may include a dowel member. In either instance, the dowel member may be inserted into the aperture.

The second spool may be moved axially along the support shaft and onto the mandrel. Then, the support member may be reassociated with the mandrel, and the loading shaft may be disassociated from the frame and the mandrel. The empty spool may be removed from the distal end portion of the mandrel by pushing first core along the mandrel with the second core.

Further to the above, the first strand may include a first end portion and a second end portion, and the second strand may include a first end portion and a second end portion. The method may further include the step of connecting the second end portion of the first strand with the first end portion of the second strand. Further still, the mandrel support member may comprise a first block member and a second block member movably connected with the frame. Thus, the step of disassociating the mandrel support member from the mandrel further includes moving the first block member and the second block member in a direction substantially perpendicular to a longitudinal mandrel axis. It is to be appreciated that in some embodiments, the mandrel support member may include an arm pivotally connected with the frame, and the step of disassociating the mandrel support member from the mandrel may include pivoting the arm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm." Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for loading material on an unwinding apparatus comprising the steps of:
    providing a mandrel including a proximal end portion and a distal end portion, wherein the mandrel is adjacent to a frame, and wherein a portion of the mandrel is associated with a mandrel support member;
    supporting a first spool on the mandrel, the first spool comprising a first core and a first strand of material wound around the first core, and wherein the first core is adapted to receive the mandrel;
    providing a second spool comprising a second core and a second strand of material wound around the second core;
    placing the second spool onto a loading shaft including a proximal end portion and a distal end portion, wherein the second core is adapted to receive the loading shaft;
    slidably engaging the loading shaft with the mandrel;
    disassociating the mandrel support member from the mandrel;
    moving the second spool axially along the support shaft and onto the mandrel;
    reassociating the support member with the mandrel; and
    disengaging the loading shaft from the mandrel;
    wherein the mandrel support member comprises an arm pivotally connected with the frame, and wherein the step of disassociating the mandrel support member from the mandrel further comprises pivoting the arm.

2. The method of claim 1, wherein the first strand comprises a first end portion and a second end portion, and wherein the second strand comprises a first end portion and a second end portion, the method further comprising the step of connecting the second end portion of the first strand with the first end portion of the second strand.

3. The method of claim 2, further comprising the step of:
    unwinding the first strand of material from the first core in a direction past the distal end of the mandrel.

4. The method of claim 1, further comprising the step of associating the distal end portion of the loading shaft with the proximal end portion of the mandrel.

5. The method of claim 4, wherein the distal end portion of the loading shaft is received within the proximal end portion of the mandrel.

6. The method of claim 1, wherein the mandrel support member comprises a first block member and a second block member movably connected with the frame, wherein the step of disassociating the mandrel support member from the mandrel further comprises moving the first block member and the second block member in a direction substantially perpendicular to a longitudinal mandrel axis.

7. The method of claim 1, further comprising the step of removing an empty spool from the distal end portion of the mandrel by pushing the first core along the mandrel with the second core.

8. The method of claim 7, wherein the empty spool is removed from the mandrel while unwinding the first strand of material from the first core in a direction past the distal end of the mandrel.

9. The method of claim 1, wherein the proximal end portion of the loading shaft is connected with a base member, and the step of slidably engaging the loading shaft with the mandrel further comprises associating the base member with the frame.

10. The method of claim 9, wherein a dowel member is connected with the base, and the frame comprises an aperture adapted to receive the dowel member, wherein the step of associating the base member with the frame further comprises the step of inserting the dowel member into the aperture.

11. The method of claim 9, wherein a dowel member is connected with the frame, and the base member comprises an aperture adapted to receive the dowel member, wherein the step of associating the base member with the frame further comprises the step of inserting the dowel member into the aperture.

12. An unwind apparatus, the apparatus comprising:
    a frame;
    a mandrel including a proximal end portion and a distal end portion, the mandrel adapted to support a spool comprising a core and a strand of material wound around the core, wherein the mandrel is adapted to be received by the core;
    a mandrel support member configured to associate with the mandrel, the mandrel support member comprising an arm pivotally connected to the frame;
    a loading apparatus for supporting a replacement spool comprising a core and a strand of material wound around the core, the loading apparatus comprising:
        a base member; and
        a loading shaft including a proximal end portion and a distal end portion, the proximal end portion of the loading shaft connected with the base member, wherein the distal end portion is configured to associate with the proximal end portion of the mandrel, and wherein the loading shaft is adapted to be received by the core of the replacement spool;
    wherein in a first configuration, the distal end portion of the loading shaft is slidably engaged with the proximal end portion of the mandrel, and wherein the mandrel support member is disassociated from the mandrel such that the core of the replacement spool is movable along the loading shaft and onto the mandrel,
    wherein in a second configuration, the distal end portion of the loading shaft is disassociated with the proximal end portion of the mandrel, and wherein the mandrel support member is associated with the mandrel.

13. The apparatus of claim 12, further comprising an aperture in the frame, and a dowel member connected with base member, wherein in the first configuration the dowel member is inserted into the aperture.

14. The apparatus of claim 12, further comprising an aperture in the base member, and a dowel member connected with frame, wherein in the first configuration the dowel member is inserted into the aperture.

15. The apparatus of claim 12, wherein the mandrel support member comprises a first block member and a second block member movably connected with the frame.

16. The apparatus of claim 12, further comprising a vacuum fluidly connected with the mandrel.

17. The apparatus of claim 12, further comprising a blade adjacent the distal end portion of the mandrel.

* * * * *